US006977597B2

(12) United States Patent
Doherty

(10) Patent No.: US 6,977,597 B2
(45) Date of Patent: Dec. 20, 2005

(54) VEHICLE MOUNTED TRAVEL SURFACE AND WEATHER CONDITION MONITORING SYSTEM

(76) Inventor: John A. Doherty, 829 St. Andrews La., Louisville, CO (US) 80027

( * ) Notice: Subject to any disclaimer, the term of this patent is extended or adjusted under 35 U.S.C. 154(b) by 106 days.

(21) Appl. No.: 10/379,119

(22) Filed: Mar. 3, 2003

(65) Prior Publication Data

US 2003/0178501 A1 Sep. 25, 2003

Related U.S. Application Data

(63) Continuation of application No. 09/953,379, filed on Sep. 14, 2001, now Pat. No. 6,538,578, which is a continuation of application No. 09/337,984, filed on Jun. 22, 1999, now Pat. No. 6,535,141, which is a continuation-in-part of application No. 09/286,809, filed on Apr. 6, 1999, now Pat. No. 6,173,904, which is a continuation of application No. 08/879,921, filed on Jun. 20, 1997, now Pat. No. 5,904,296, which is a continuation-in-part of application No. 08/783,556, filed on Jan. 14, 1997, now Pat. No. 5,745,051, which is a continuation of application No. 08/660,232, filed on Jun. 7, 1996, now Pat. No. 5,619,193.

(60) Provisional application No. 60/000,040, filed on Jun. 8, 1995, provisional application No. 60/004,941, filed on Oct. 6, 1995, provisional application No. 60/020,237, filed on Jun. 2, 1996, and provisional application No. 60/031,036, filed on Nov. 18, 1996.

(51) Int. Cl.[7] ............................................... G08G 1/09
(52) U.S. Cl. ....................... 340/905; 340/580; 340/581
(58) Field of Search ................................ 340/905, 988, 340/580, 581, 583, 603, 436; 324/642, 644; 356/51, 448; 701/50, 213, 215; 404/84.05, 84.1, 84.5, 102

(56) References Cited

U.S. PATENT DOCUMENTS 3,160,964 A    12/1964  Boyer et al. ................ 239/684
3,519,169 A    7/1970   Holland ....................... 222/626
3,540,655 A    11/1970  Hinrichs ....................... 239/75

(Continued)

FOREIGN PATENT DOCUMENTS

| CA | 2060418 | 8/1993 |
|---|---|---|
| CA | 2233689 | 4/1997 |
| FR | 2618543 | 7/1987 |

OTHER PUBLICATIONS

Brochure, "425 Ultrasonic Wind Sensor", Jun. 14, 1996.
Article, "Magnetic strips make snow ploughs smarter", ITS: Intelligent transport systems, Jan./Feb. 1997.
Article, "ITS applications for magnetic tape", ITS: Intelligent transport systems, Jan./Feb. 1997.

(Continued)

*Primary Examiner*—Van T. Trieu
(74) *Attorney, Agent, or Firm*—Lathrop & Gage, L.C.

(57) ABSTRACT

A system and apparatus for detecting and evaluating surface conditions on a road surface and atmospheric conditions simultaneously from a vehicle is disclosed. The system comprises a sensor for detecting the presence of deposited material on a road surface, a detector for determining one or more characteristics of the deposited material such as freezing temperature, process means for converting a detected signal and display means for displaying the condition of the road surface, and a sensor for detecting falling precipitation. An embodiment of the present invention includes a remote sensing apparatus which utilizes electromagnetic radiation to sense actual surface material conditions, temperatures, and composition and local atmospheric conditions at the vehicle as it is moving over a travel surface. This information is then processed through a computer in order to determine those additional steps necessary to apply additional materials to the road surface in order to minimize hazardous driving conditions.

20 Claims, 19 Drawing Sheets

U.S. PATENT DOCUMENTS

| | | | |
|---|---|---|---|
| 3,655,130 A | 4/1972 | Patrick | 239/77 |
| 3,856,206 A | 12/1974 | Bell et al. | 239/75 |
| 3,891,979 A | 6/1975 | Braun et al. | 340/581 |
| 3,995,569 A | 12/1976 | Picardat | 239/656 X |
| 4,052,003 A | 10/1977 | Steffen | 239/71 |
| 4,077,139 A * | 3/1978 | Fagervold et al. | 37/280 |
| 4,084,748 A | 4/1978 | Anderson et al. | 239/74 |
| 4,176,791 A | 12/1979 | Cattaneo et al. | 239/76 |
| 4,209,065 A | 6/1980 | Ledent | 166/64 |
| 4,210,284 A | 7/1980 | Tarnay et al. | 239/75 |
| 4,230,280 A | 10/1980 | Leigh et al. | 239/677 |
| 4,274,091 A | 6/1981 | Decker | 340/905 |
| 4,373,668 A | 2/1983 | Forbes et al. | 239/74 |
| 4,422,562 A | 12/1983 | Rawson | 222/55 |
| 4,442,979 A | 4/1984 | Kupper | 239/656 |
| 4,491,275 A | 1/1985 | Holsworth | 239/687 X |
| 4,492,952 A | 1/1985 | Miller | 340/52 F |
| 4,503,806 A | 3/1985 | Prusak et al. | 118/712 |
| 4,523,280 A | 6/1985 | Bachman | 364/424 |
| 4,529,336 A | 7/1985 | Shinozaki et al. | 406/14 |
| 4,553,702 A | 11/1985 | Coffee et al. | 239/690 |
| 4,577,781 A | 3/1986 | Braun | 222/54 |
| 4,588,127 A | 5/1986 | Ehrat | 239/662 X |
| 4,678,056 A | 7/1987 | Kobari et al. | 180/247 |
| 4,684,062 A | 8/1987 | Bagwell | 239/1 |
| 4,690,553 A | 9/1987 | Fukamizu et al. | 340/583 |
| 4,700,223 A | 10/1987 | Shoutaro et al. | 358/93 |
| 4,700,895 A | 10/1987 | Takata | 239/664 |
| 4,733,760 A | 3/1988 | Inagaki et al. | 192/3 |
| 4,768,716 A | 9/1988 | Buchanan, Jr. et al. | 239/284.1 |
| 4,803,626 A | 2/1989 | Bachman et al. | 364/424.07 |
| 4,805,088 A | 2/1989 | Cross et al. | 364/172 |
| 4,809,197 A | 2/1989 | Tashiro et al. | 364/550 |
| 4,955,538 A | 9/1990 | Laube et al. | 239/1 |
| 4,984,163 A | 1/1991 | Kuwana et al. | 364/426.02 |
| 5,012,977 A | 5/1991 | Karklins et al. | 239/284.1 |
| 5,028,017 A | 7/1991 | Simmons et al. | 244/134 C |
| 5,069,392 A | 12/1991 | Wise et al. | 239/675 |
| 5,096,125 A | 3/1992 | Wise et al. | 239/675 |
| 5,186,396 A | 2/1993 | Wise et al. | 239/675 |
| 5,267,696 A | 12/1993 | Balmer | 239/662 |
| 5,310,113 A | 5/1994 | Cowgur | 239/69 X |
| 5,318,226 A | 6/1994 | Kime et al. | 239/687 X |
| 5,343,744 A | 9/1994 | Ammann | 73/170.13 |
| 5,366,039 A | 11/1994 | Sawada | 180/197 |
| 5,416,476 A | 5/1995 | Rendon | 340/905 |
| 5,447,272 A | 9/1995 | Ask | 239/7 |
| 5,449,049 A | 9/1995 | Every | 180/197 |
| 5,452,966 A | 9/1995 | Swisher, Jr. | 404/72 |
| RE35,100 E | 11/1995 | Monson et al. | 111/130 |
| 5,515,623 A | 5/1996 | Weeks | 239/289 X |
| 5,521,594 A | 5/1996 | Fukushima | 340/905 |
| 5,619,193 A | 4/1997 | Doherty et al. | 340/905 |
| 5,652,522 A | 7/1997 | Kates et al. | 324/644 |
| 5,653,389 A | 8/1997 | Henderson et al. | 239/172 X |
| 5,684,476 A | 11/1997 | Anderson | 340/988 |
| 5,699,056 A | 12/1997 | Yoshida | 340/905 |
| 5,745,051 A | 4/1998 | Doherty et al. | 340/905 |
| 5,746,539 A * | 5/1998 | Mara | 404/84.05 |
| 5,774,070 A | 6/1998 | Rendon | 340/905 |
| 5,796,344 A | 8/1998 | Mann et al. | 340/583 |
| 5,818,339 A * | 10/1998 | Giles et al. | 340/583 |
| 5,904,296 A | 5/1999 | Doherty et al. | 239/663 X |
| 5,928,504 A | 7/1999 | Hembre et al. | 218/88 |
| 5,931,393 A | 8/1999 | Alsip et al. | 239/677 X |
| 5,931,882 A | 8/1999 | Fick et al. | 701/50 |
| 5,947,931 A | 9/1999 | Bierman | 239/677 |
| 5,955,973 A | 9/1999 | Anderson | 340/988 |
| 5,957,621 A | 9/1999 | Clark, Jr. et al. | 404/111 |
| 6,089,743 A | 7/2000 | McQuinn | 364/479.1 |
| 6,092,745 A | 7/2000 | Seymour et al. | 239/675 |
| 6,173,904 B1 | 1/2001 | Doherty et al. | 239/1 |
| 6,236,907 B1 | 5/2001 | Hauwiller et al. | 700/283 |
| 6,246,938 B1 * | 6/2001 | Giletta et al. | 701/50 |
| 6,354,786 B1 | 3/2002 | Feller | 414/489 |
| 6,377,881 B1 * | 4/2002 | Mullins | 701/50 |
| 6,535,141 B1 | 3/2003 | Doherty | 340/905 |
| 6,538,578 B1 | 3/2003 | Doherty | 340/905 |
| 2004/0195357 A1 | 10/2004 | Doherty et al. | |

OTHER PUBLICATIONS

Article, "UK proposes three private traffic control centres", ITS: Intelligent transport systems, Jan./Feb. 1997.
Article, "Crash warning system set for sale in Europe and Japan", ITS: Intelligent transport systems, Jan./Feb. 1997.
Advertisement, Root Snow Plows.
Mobile GPS Builds on 7400 Technology to Claim the Future of Pavement Management, FactsFinder.
Advertisement, Henderson Manufacturing Reversible Plow.
Advertisement, Henderson Manufacturing Patrol Wing.
Advertisement, Tenco Side Wings.
Advertisement, Tenco Reversible Plow.
Surveyors Use Pedal Power to Map City, ENR, Nov. 13, 1995.
Trimble, AEC Automation Newsletter, Sep. 1995.
GPS Satellites, Trimble Precise Positioning Systems.
GPS Goes Real Time, Civil Engineering, Sep. 1994.
Advertisement, Vibro–Meter SA, Fribourg, Switzerland.
Scan FP 2000 Sensor Advertisement, Surface Systems Inc.
Data Sheet D251, Aanderaa Instruments, Mar. 1995.
UCRL–MI–120916, Lawrence Livermore National Laboratory, Jun. 7, 1995.
Article, "Calibration to Automation", Road & Bridges, Jun. 1999.
Block diagram from Iowa Department of Transportation presentation, Aug. 11, 1999.
Advertisement, Compu–Spread™ "Introducing our On board Liquid Pre–Wetting System. C.I.S.—SERIES," Appears to be available as early as Apr. 1997.
GL 400 Spreader Control Presentation, Component Technology, Appears to be available as early as Mar. 15, 2001.
White Paper, "Ice! Alert," Appears to be available as early as 1998.
"SaltMiser™ Operating Instructions," Dec. 8, 1997.
Marketing Document, DIDACTICS Incorporated, "Why SaltMiser?," pp. 1,3, and 5 of 6 available.
Marketing Document, DIDACTICS Incorporated, "Saltmiser™ 2.0 A Real Time Salt Application Controller," Oct. 25, 1997.
Marketing Document, DIDACTICS Incorporated, "IR Applications for Ice and Snow Control," pp. 335–362 available, Appears to be available as early as May 12, 1998.
Brochure, Enator Telub AB, "Mobile Road Condition Monitoring," Appears to be available as early as 1998.
Article, "Better bridge deicing on the way?" Better Roads, Jun. 1995.
Advertisement, Passport 5000, "Only Passport 5000 Gives You the Total Picture," 1995.
Article, "Roads Report," edited by Larry Flynn, Roads & Bridges, Mar. 1993.
Article, "Americans can Learn a Lot from European, Japanese Snowfighters," by Leland D. Smithson, P.E., Roads & Bridges, pp. 30–32 available, Jun. 1995.
Article, "Developments Improve Road Weather Information Systems," Betters Roads, pp. 21 and 24 available, Oct. 1995.

Draft Proposal, Policy Recommendations to the RAQC Concerning the Comprehensive Long Range Air Quality Plan, from the Street Sanding/Cleaning Subcommittee City of Aurora Public Works Dept. (Colorado), Nov. 1, 1995.

Article, "RWIS helps with snow and ice control," Better Roads, Sep. 1994.

Brochure, Tell Temp 750, Geneva Scientific, Oct. 1994.

Brochure, "Artificial Intelligence/Expert Systems," Kaman Sciences Corporation, Copyright 1991.

Article, "Traffic Sensor System," Better Roads, Dec. 1995.

Article, "The View From Space Satellites keep eye on earthly activity," USA Today.

Article, "Riding the Data Highway," Newsweek, p. 97, Mar. 21, 1994.

Picture diagram, "One–Second Emissions Test," Denver Post, May 7, 1995.

Article, "Colorado Hosts Pilot Workshop Pavement Preventive Maintenance: An Idea Whose Time Has Come," Focus, US Department of Transportation Federal Highway Administration, Aug. 1995.

Article, "Innovations in ITS," ITE Journal, Dec. 1996.

Brochure, "KEMS . . . A Geographic Information System Tailored for Emergency Management Applications," Kaman Sciences Corporation.

Article, "Measuring Salt's Effectiveness in New York," Better Roads, Jan. 1995.

Excerpts from America Online: KKlean, Jun. 30, 1995.

Article, "Clementine Searches for Ice on Moon," by Jane E. Allen, Sunday Camera, Apr. 17, 1994.

Article, entitled "Cellular technology has new niche, Phones offer mobile control in rural Colorado," by Dinah Zeiger, Denver Post, Aug. 21, 1994.

Article, "Columbia/HCA system speeds test result delivery," USA Today, Nov. 11, 1994.

Article, "Danger—Black Ice!" Traffic Technology International, 1994.

Article, "New Horizons at Harris," by Bernie Ward, Sky, Dec. 1994.

Kaman Annual Report, 1993.

Article, "Humidity and Pressure Measurement," Vaisala News, 1992.

Kaman, A Technology Company, Fact Book, 1993.

Article, "The Snow on Pluto," by Jeffrey Winters, Discover, Jan. 1997.

Article, "Water, Pure and Simple," by Ashok Gadgil, Discover, pp. 87–88, Jul. 1996.

Article, "One Very Cold Lake," by Kathleen Spiessbach, Discover, p. 26, Jan. 1997.

Article, "Perpetual Flight," by Kathy A. Svitil, Discover, p. 38, Nov. 1996.

Advertisement, Cole–Parmer Instrument Company, re: Cole–Parmer Low–Cost Infrared Thermometers, 1997.

Brochure, Southwest Research Institute—Guide, 13 pages, Aug. 1996.

Brochure, Southwest Research Institute—Guide, 13 pages, Jan. 1998.

Brochure, "Facts About Southwest Research Institute," Southwest Research Institute, San Antonio, Texas.

Annual Report from Southwest Research Institute, 1996.

Annual Report from Southwest Research Institute, 1997.

Feedback on article, "Managing Winter Weather" and "Visibility a Key Component of Weather Systems," by John D. Crosby, Dec. 1996.

Article, "Ordinary Vinegar Found Among Stars," by Paul Recer.

Brochure, "Solving Today's Problems for Tomorrow's Safety," Control Products, Inc.

Advertisement, "Are You Still Detecting Icy Roads Between Pavement Sensors by the Seat of Your Pants?" Vaisala.

Brochure, "Better Roads . . . Safer Roads . . . More Cost Effective Roads . . . Through Innovations in Technology," Federal Highway Administration.

Article, "Sensors to Help State Keep Ahead of Storms," by Ed Vogel.

Brochure, "Autoscope," Econolite Control Products, Inc.

Brochure, "Playing with Fire—Science and Politics of Air Pollution from Cars".

Article, "Out Front—What's Happening in the World of ITS".

Article, "New Auto Technology Helps Guide Drivers, Avoid Crashes," by Earle Eldrige, USA Today.

Advertisement, "Hand–Held Autoranging Conductivity Meters".

Instruction Manual from Coralba ad, Sweden, "Instructions for C–u Friction Tester".

Viking '79 Rover Study Final Report, vol. I, Summary, vol. II, Detailed Technical Volume, NASA CR–132417, Martin Marietta Corporation, Mar. 1974.

* Article, "Just Drive!," by Allen Zeyher, Roads & Bridges, Apr. 2002.

* cited by examiner

VEHICLE MOUNTED TRAVEL SURFACE AND WEATHER CONDITION MONITORING SYSTEM

CROSS REFERENCE TO RELATED APPLICATIONS

This application is a continuation of U.S. patent application Ser. No. 09/953,379, filed on Sep. 14, 2001, now U.S. Pat. No. 6,538,578, which is a continuation of U.S. patent application Ser. No. 09/337,984, filed on Jun. 22, 1999, now U.S. Pat. No. 6,535,141, which is a continuation-in-part of U.S. patent application Ser. No. 09/286,809, filed on Apr. 6, 1999, now U.S. Pat. No. 6,173,904, which is a continuation of U.S. patent application Ser. No. 08/879,921, filed Jun. 20, 1997, which also claims the benefit of U.S. Provisional Patent Applications Ser. Nos. 60/020,237, filed Jun. 21, 1996, and 60/031,036, filed Nov. 18, 1996, now U.S. Pat. No. 5,904,296, which is a continuation-in-part of U.S. patent application Ser. No. 08/783,556, filed on Jan. 14, 1997, now U.S. Pat. No. 5,745,051, which is a continuation of U.S. patent application Ser. No. 08/660,232, filed Jun. 7, 1996 and now U.S. Pat. No. 5,619,193, which also claims the benefit of U.S. Provisional Patent Applications Ser. Nos. 60/000,040, filed Jun. 8, 1995, and 60/004,941, filed on Oct. 6, 1995, each of the above-identified related applications and patents are hereby incorporated by reference in their entirety as though fully set forth herein.

BACKGROUND OF THE INVENTION

1. Field of the Invention

This invention relates generally to the field of vehicle travel surface condition monitoring and control systems, and more particularly to a vehicle mounted and/or stationary positioned system for determining characteristics of surface materials related to adverse driving conditions which includes a vehicular mounted weather monitoring subsystem for measuring weather conditions at the vehicle location.

2. Description of the Related Art

Stationary weather stations have weather vanes and wind velocity meters to provide wind direction and speed information (velocity), and sensors to provide relative humidity, air temperature, and precipitation amounts and rates, among other parameters, to local and remote locations. Some aircraft also have been equipped with similar equipment to monitor conditions in thunderstorms and hurricanes. However, such instrumentation has commercially not been installed on motor vehicles.

Road condition service vehicles such as snow plow trucks and surface conditioning vehicles which deposit materials such as sand and chemicals such as salt to travel surfaces depending on the current or predicted road surface conditions do not carry weather analysis equipment on board. Proper surface conditioning materials are optimally applied during the early stages of adverse weather conditions as well as throughout the adverse weather condition. However, the optimal distribution of materials and compositions change dramatically as the storm progresses through a locality. Currently there is no real time weather sensing apparatus available that can be vehicle mounted which determines weather conditions such as wind speed and direction, temperature, humidity, precipitation events, water content and rates of deposition, and barometric pressure.

A number of attempts have been made to sense the conditions of roadways, aircraft runways, and other surfaces for vehicular traffic, during changing adverse weather conditions For example, it is known to place conductivity, temperature and other sensors either in the road surface or adjacent the road to monitor the temperature of the road surface, the subsurface temperature and/or monitor whether there is ice forming on the surface. Atmospheric sensors may also be provided adjacent the road. This information can then be fed to a central location for control and dispatch of trucks to apply salt or sand or other deicing mixtures. At airports these types of warning systems are used to inform maintenance crews that the runways need to be treated or alert the staff that deicing procedures need to be implemented. Some conventional systems have a supply of chemicals and pumps beside the roadway or runway to automatically spray the road when triggered by a sensor.

There is also a need for such a warning system on road vehicles such as cars, buses and trucks to detect pending adverse conditions. However, available mobile systems are limited to basic moisture detection and temperature monitoring systems. Some examples of such systems are disclosed in U.S. Pat. Nos. 4,492,952 and 4,678,056. One particular system, disclosed in U.S. Pat. No. 5,416,476, employs an infrared sensor which is mounted on the exterior of the vehicle and sends a signal to a microprocessor which then can display the temperature of the road surface. These systems are simplistic and do not tell the operator the critical information needed under all conditions, such as, what is the composition of and at what temperature will the particular material actually on the road surface freeze? Therefore there is a need for an on board material sensing apparatus and system for determining when an actual liquid on a road surface will freeze in view of current weather conditions at the vehicle location and alerting the operator to such adverse driving situations before they actually occur so that the operator can adjust material spreading techniques and strategies accordingly.

There is also a need for a mobile mounted sensing apparatus and system for use by road crews to evaluate current local weather conditions and determine and evaluate existing materials, if any, on a road surface in order to determine the optimumal amount, type and timing of additional material to be applied to the surface in order to reduce the current and future hazardous driving conditions.

There is also a need for an apparatus and system for predicting, displaying and sometimes controlling the distribution of travel surface conditioning materials available on board local road crew trucks based on current and predicted local weather conditions at the travel surface location. Such a system is unavailable today.

SUMMARY OF THE INVENTION

The system in accordance with the present invention addresses the above described needs. It is thus an object of the present invention to provide a unique multipurpose system which includes a vehicle mounted surface monitoring portion and/or a weather condition monitoring portion. In addition, the system preferably includes a fixed or mobile system for receiving and/or measuring weather conditions at vehicle locations and predicting and forecasting future travel surface conditions to provide recommendations for and verification of surface conditioning activities and results.

The surface monitoring portion may include a multipurpose sensor mounting platform accommodating a variety of sensors that enables the temporary use of materials such as surface water and road conditioning materials actually encountered on a road surface to determine the condition of the road surface. It is another object of the invention to provide a system for remotely detecting the actual materials and/or characteristics of materials on a roadway and determining a characteristic such as friction coefficients, chemical composition or the actual freezing temperature of a material on a road surface regardless of the makeup of the material or depth of the material.

It is a still further object of the present invention to provide a reliable display of information to the vehicle operator of actual and pending conditions of the road surface. It is a still further object of the invention to provide an apparatus for sensing actual road conditions that can function automatically or manually and which permits automatic or manual control of distribution of on board conditioning materials.

It is a still further object of the present invention to provide a system for remote sensing and evaluation of material present on a roadway surface which includes a means for extracting sufficient information to determine the characteristics of the composition of the surface material and utilizing user input information as well as local weather conditions at the vehicle location, as well as at fixed locations, to calculate the amount of additional material, if any, and what type, to be applied to the road surface to mitigate the development of future adverse conditions. This may involve utilization of look up tables, of historical data for the location, continual updating of such tables with actual data from the location, and utilization of algorithms for predicting future conditions at the site.

Throughout this specification, the term "vehicle" is meant inclusively to refer to any moving vehicle, whether it be a land vehicle such as a salt truck or an airborne or orbital vehicle such as an airplane or satellite. The sensing portion of the system of the present invention may be adapted for mounting and operation on any such vehicle. The vehicle referred to with respect to carrying and distributing surface conditioning materials typically is a truck.

One embodiment of the apparatus for sensing surface material condition in accordance with the present invention comprises a collection means for receiving material discharged, for example, from a vehicle wheel in contact with a roadway surface, at least one sensing means coupled to the collection means for detecting a characteristic of the received material such as friction coefficients, temperature, conductivity, and chemical concentrations and producing a corresponding signal, processing means for converting the corresponding signal, and display means connected to the processing means for providing an indication of surface conditions based on the material characteristics.

The collection means may include a modified mud flap located immediately behind a vehicle wheel so that a portion of any surface material that is picked up by the vehicle wheel and thrown toward the flap may be collected. An alternative collection means is a scoop located in proximity of the wheel or adjacent the road surface to collect deposited surface material. Another alternative is a separate sensor wheel contacting the vehicle travel surface which has sensors mounted thereon or therein for analyzing the deposited surface materials.

Another embodiment of the surface monitoring portion of the invention does not require a collection means, but instead, remotely senses directly the surface material characteristics such as temperature, conductivity, friction coefficients or chemical concentrations. This embodiment utilizes a sensor or series of sensors located on the undercarriage of the vehicle at a preferably fixed distance from the road surface which senses the surface temperature and at least one other unique surface material characteristic so that the specific material or materials can be identified, the composition determined, and freezing temperatures determined. This embodiment may also include a subsurface radar or other electromagnetic radiation transceiver directed at the ground for determining road surface temperature when the roadway is ice or snow covered and determining the temperature of the underlying ground beneath the vehicle travel surface.

Another embodiment of the apparatus has a sensor mud flap which includes a channel leading into a detection chamber where liquid runoff from the wheel flap is periodically collected and then frozen. The freeze point is sensed along with the temperature of the incoming material. The freeze point may be determined as the collected material changes from liquid to solid or as the material changes from solid to liquid during thawing of a sample. This freeze point information is displayed to the operator of the vehicle. Once the freeze point is determined, the frozen material is fully thawed and discharged from the chamber so that a new sample may be collected and analyzed.

Another embodiment of the surface material monitoring portion of the present invention includes an endless belt of liquid absorbing material mounted to the flap. The endless belt collects and absorbs liquid collected by the flap, transports it to a collector which extracts the liquid from the belt and directs it to the sensor means which also can be a detection chamber where the chamber contents is frozen in order to sense the freeze point.

The sensing means may be a single sensor or a combination of several sensors to detect particular parameters of interest. The road conditions are primarily affected by changes in temperature, wind, dew point, and material concentrations. Therefore the sensing means may include resistance temperature detectors, thermocouple, infrared temperature sensors, conductivity detectors, close proximity electromagnetic radiation (EMR) transmitters and detectors or transceivers, friction measurement devices, and other material analysis systems such as a spectrographic analysis system such as a mass spectrometer or laser induced breakdown spectrometer. In the latter case, the mass spectrometer or other material analysis device would preferably be mounted inside the vehicle, with a sample conveying means such as a belt or pump line directing the sample from the flap or other collection platform such as a scoop, etc. into the analysis device, e.g., the vaporizing chamber for the spectrometer. Alternatively, an ultra wide band Doppler radar or any other suitable electromagnetic radiation (EMR) emission and detection technique as well as Laser Induced Breakdown Spectroscopy (LIBS) looking directly at the material on the road surface may be used to remotely ascertain chemical and physical characteristics of the material on the roadway surface. As another alternative, several of the above sensing devices could be directed toward materials still on the travel surface, on a moving belt, moving past the sensor, or flying through the air.

The processing means may include a microprocessor for converting sensed signals to display signals, store potential material data, determining material identity and pertinent material characteristics, and includes power and signal transmission means. This processing means can be located in several locations, including in the vehicle or remote from the vehicle The display means may be a panel with indicators of the freeze point, the ambient temperature, and other meteorological characteristics as well as surface material characteristics, and connections to more detailed signal analysis equipment such as chart recorders, tape recording devices, or other processing equipment. The display means may also include suggested remediation actions, alarms and inputs to automatic functions such as activating anti-lock brake systems, or transfers from two wheel to all-wheel drive systems, or activating chemical spreader control functions.

The weather monitoring portion of the system in accordance with the present invention preferably includes a microcomputer connected to various inputs which may include a Global Positioning System (GPS) receiver to provide vehicle location, altitude, direction of motion, and speed, a vehicle speedometer input to provide primary or backup speed input, a directional (upwardly, horizontally, or any appropriately directed short range electromagnetic radiation transceiver for remotely sensing the presence of precipitation and determining its type and moisture content, a wind velocity sensor, a barometric pressure sensor to provide pressure and altitude information, a relative humidity sensor, and an air temperature sensor. These sensors are each preferably connected to a processor for determining the characteristic or connected directly to a vehicle mounted computer. The surface monitoring portion and weather monitoring portion or portions preferably feed the computer and database in the overall system to generate commands to provide optimum dispensation of materials to the vehicle travel surface. These and other objects, features, and advantages of the system and apparatus of the present invention will become more apparent from a reading of the following detailed description when taken in conjunction with the accompanying drawing figures.

DETAILED DESCRIPTION OF THE INVENTION

Overall Monitoring System

Figure 9:
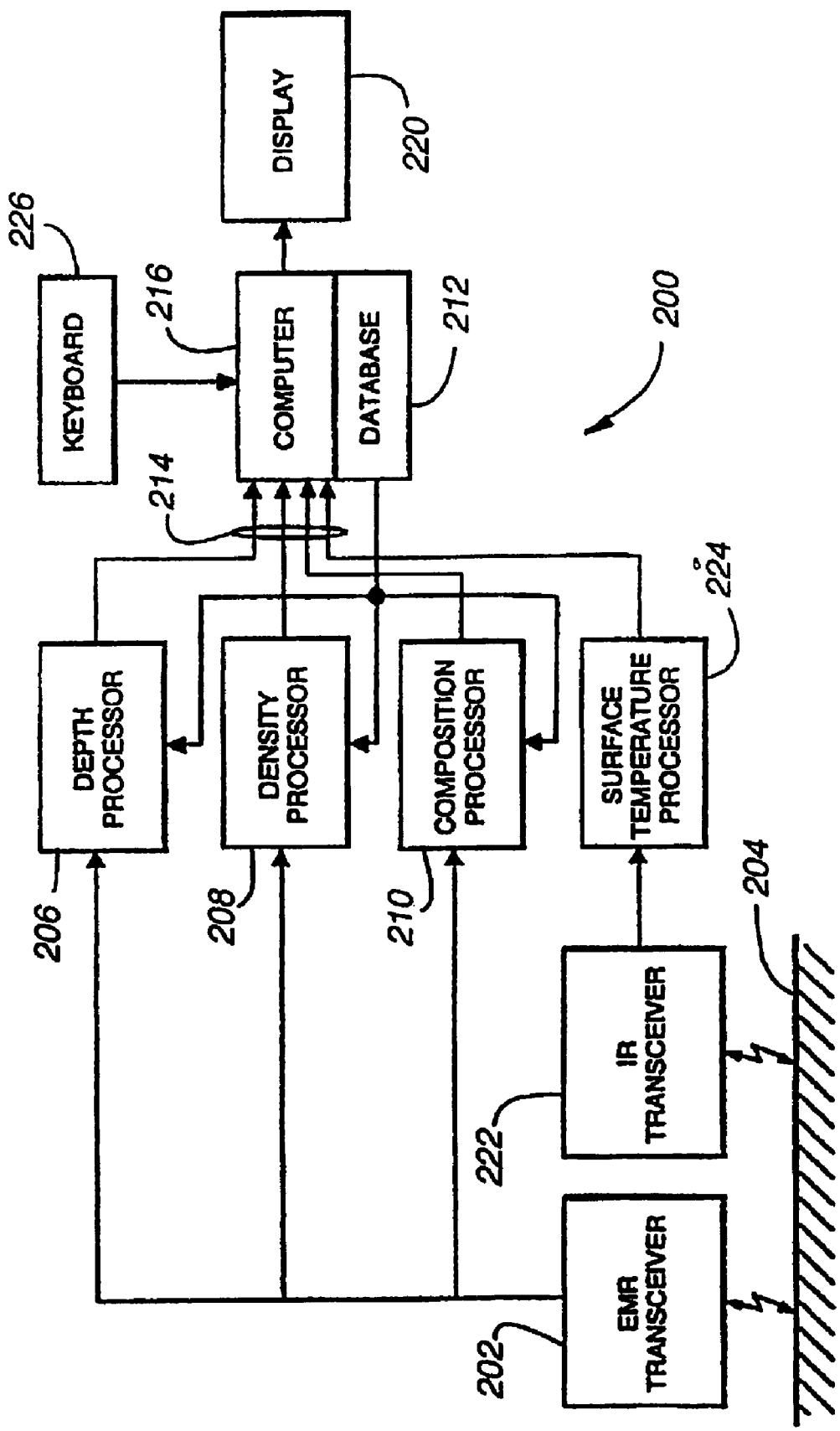
FIG. 9 is a block diagram of a remote sensing embodiment of the vehicle travel surface monitoring portion of the system in accordance with the present invention.

The system in accordance with the present invention is illustrated with reference to one embodiment in block diagram form in FIG. 11. The system 300 includes a vehicle travel surface monitoring portion 302 such as one of the systems described immediately below, preferably system 200, as is shown in FIG. 9, combined with a weather monitoring portion 304. The weather monitoring portion 304 is described in more detail following the description of the travel surface monitoring portion 302. Portions 302 and 304 have outputs which are combined in a central processor 306 which could utilize a database 308 of historical data and parametric data to determine real time potential for road surface material reaching the freeze point due to the effects of, among others, wind chill, moisture type and moisture content, chemical composition, surface and subsurface temperature and moisture accumulation. The computer and database are then utilized to determine optimum amounts of available conditioning materials present on the vehicle 10 and needed on the surface to achieve the desired results, e.g., achieve a desired level of service, or subsequently available via another vehicle, to apply to the vehicle travel surface depending on actual road conditions, local weather, and historical experience data and displays these recommendations and/or automatically controls material application to the vehicle travel surface.

Figure 14:
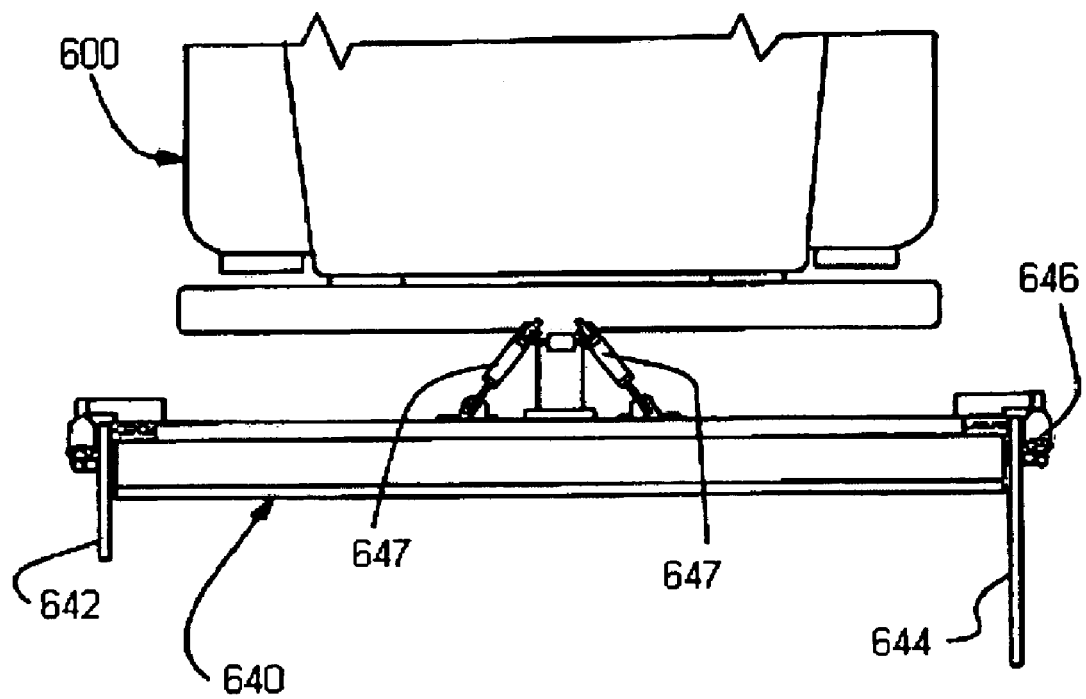
FIG. 14 is a schematic plan view of an adjustable snowplow assembly on a road service vehicle in accordance with the invention.
Figure 15:
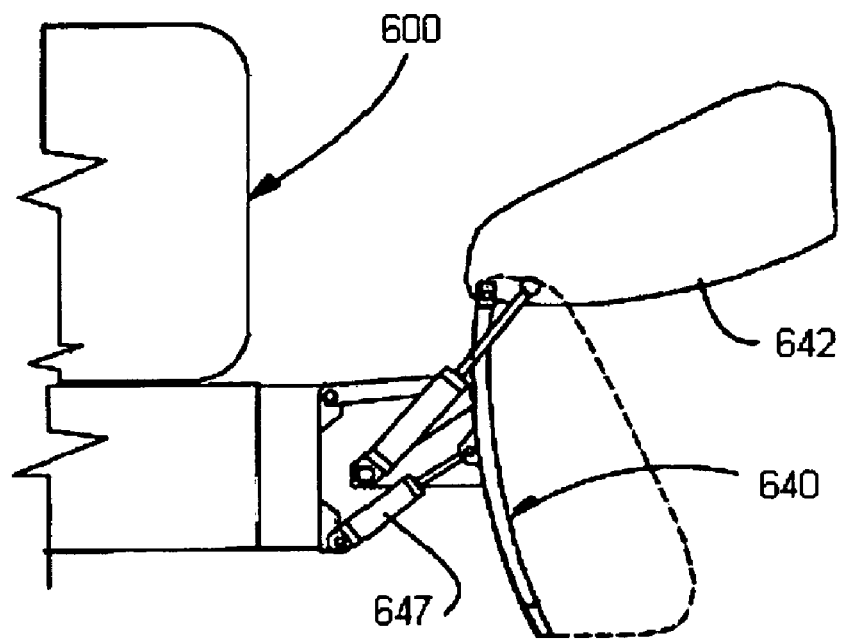
FIG. 15 is a schematic side view of the snowplow assembly shown in FIG. 14.

A snow plow 640, shown mounted on a vehicle 600 in a schematic plan view in FIG. 14, and, in a side view in FIG. 15, may also be provided that has at least one movable side discharge blocking plate 642 which is power operated, either hydraulically, electrically, or pneumatically, to raise the blocking plate 642 to permit side discharge of snow or lowered to prevent discharge of snow as the vehicle 600 passes a feature such as a residential driveway. The plow 640 may also be fitted with at least one extensible blade 644, preferably on the opposite end of the plow 640 from that carrying the blocking plate 642 which can be automatically extended or retracted in width via a hydraulic cylinder 646 depending upon the lane width at a particular location. The extensible blade 644 may be horizontally translated back and forth to extend the blade or it may be pivotally connected to the plow 640 and rotated to extend the plow path. The plow 640 may be pivoted left or right or raised and lowered by multiple cylinders 647.

Vehicle Travel Surface Monitoring Portion

First Embodiment

Figure 1:
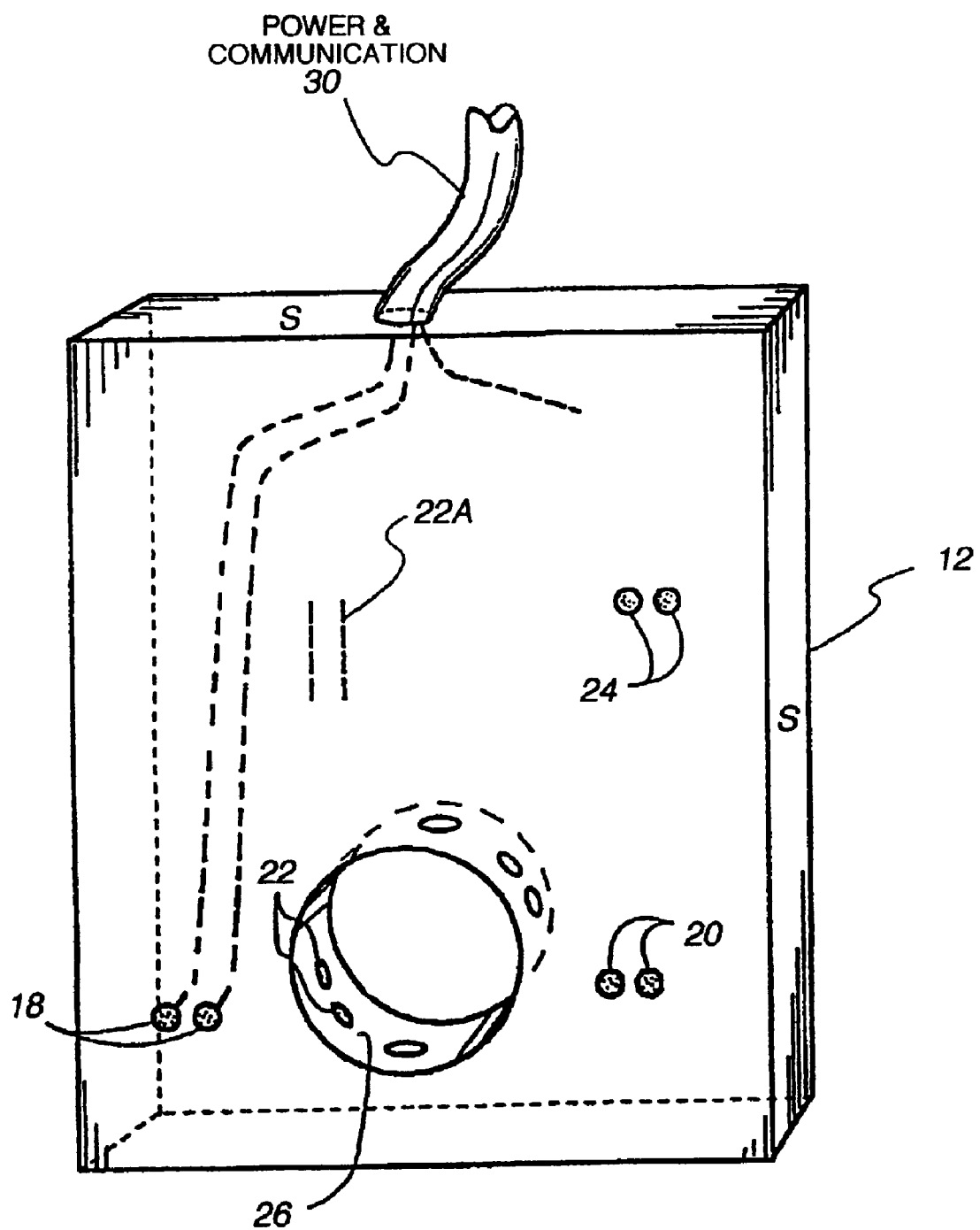
FIG. 1 is a perspective schematic view of a sensor platform in accordance with a first embodiment of the vehicle travel surface material sensing portion of the present invention.
Figure 2:
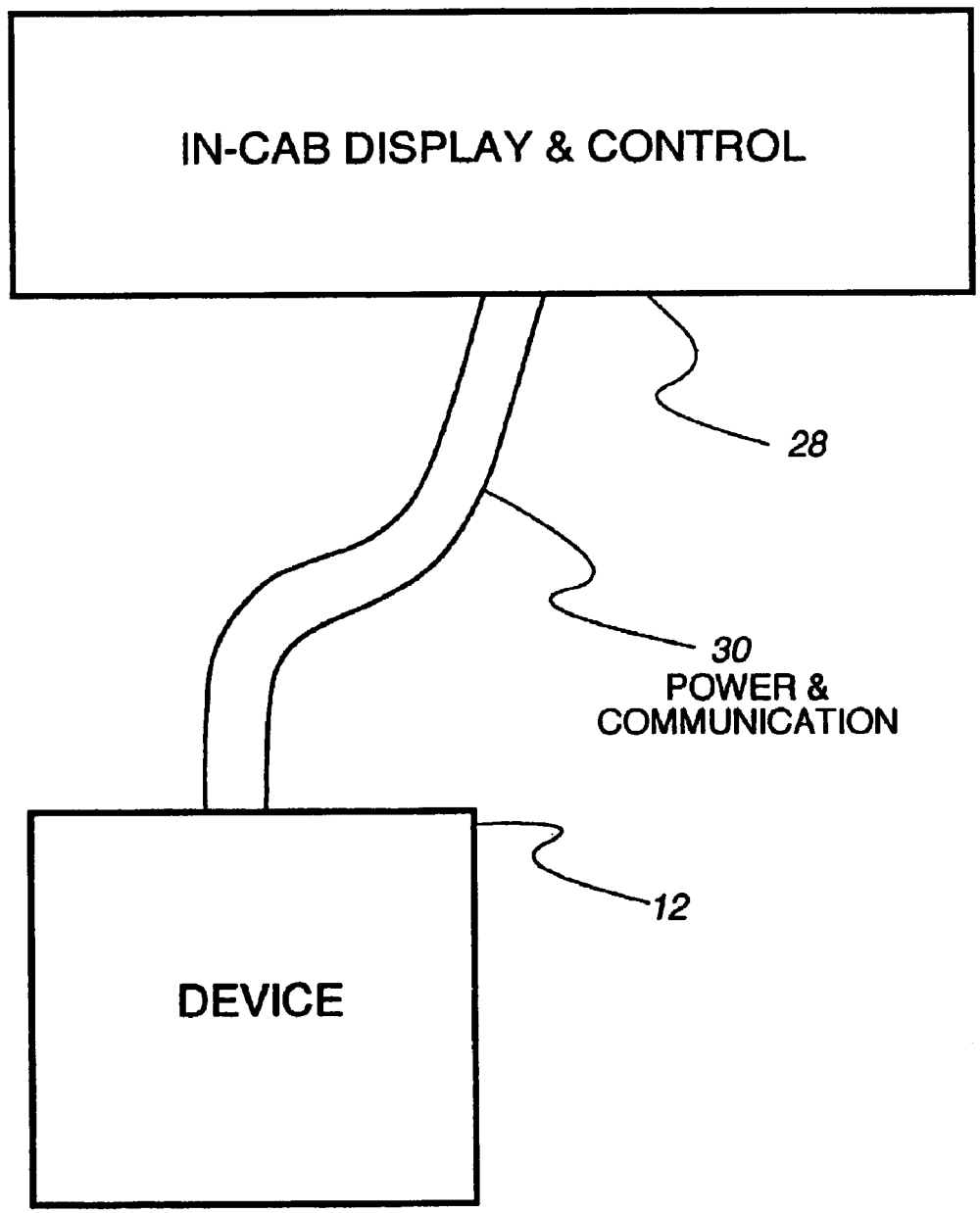
FIG. 2 is a block diagram of the first embodiment of the vehicle travel surface material sensing portion of the system in accordance with the invention.
Figure 3:
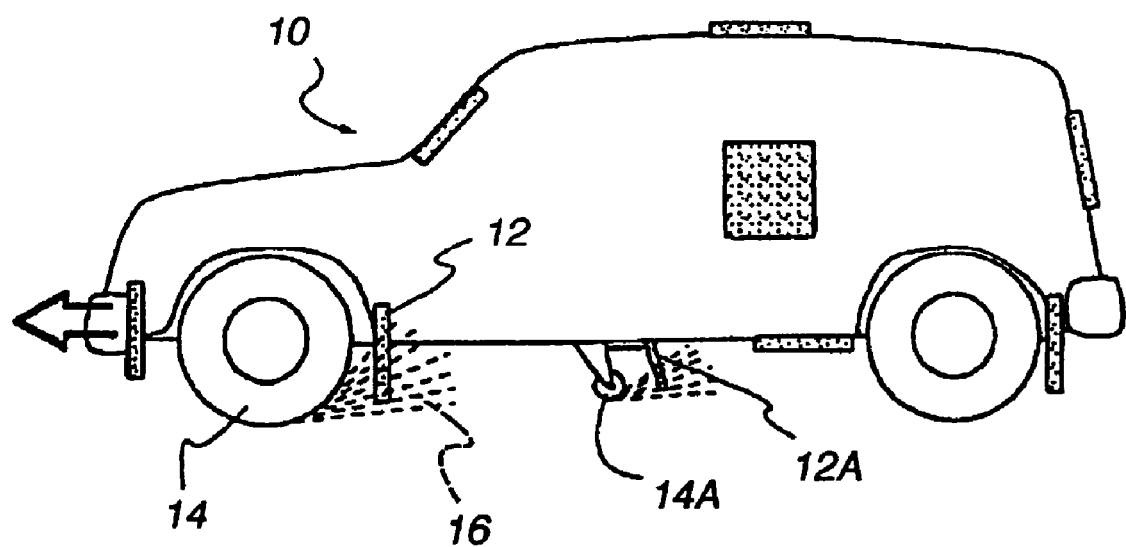
FIG. 3 is a schematic side view of a vehicle showing potential locations for the sensor platform in accordance with the present invention.

Referring now to FIGS. 1 through 3, a first embodiment of the apparatus of the invention includes a platform 12 which is typically vertically mounted behind a vehicle wheel 14 for the surface material monitoring portion if the present invention. in this application, the platform 12 replaces and also operates as a conventional mud flap on the vehicle 10.

A similar platform for the atmospheric monitoring portion of the present invention may be mounted in various positions as shown on the upper portions of the vehicle 10 in FIG. 3.

As stated above, one of the objects of this portion of the invention is to provide a unique multipurpose mounting platform 12, such as is shown in FIG. 1, that enables the temporary use of materials 16 or periodic examination of materials which are typically discharged from a vehicle wheel/road surface interface to measure certain characteristics of the materials that have left a roadway surface (surface materials), and to also determine certain characteristics of the surface itself. The surface is most commonly a road, aircraft runway surface, or farm field. Throughout this specification, use of the terms surface, road, roadway, farm field, or runway are interchangeable and are used to generally mean any surface upon which a vehicle is operated or is operable.

The manipulation of the characteristics of surface materials, for instance freezing the surface material, is one efficient and accurate way to obtain information on the surface conditions as well as determine the conditions of loose surface material.

The characteristics to be measured may include but are not limited to:
1. Material volumetric buildup, such as snow, ice, liquid solution, i.e., depth of material on the surface.
2. Determination of the constituents of the chemical solutions and mixtures present, and characteristics of the solutions and mixtures, such as percent of a particular chemical in solution, the freezing point (temperature) of the total solution or mixture, and the amount or percentage of a component in the solution and/or mixture.
3. Temperatures, both ambient and of the material solution or mixture sensed.
4. Friction characteristics.

The methodology of determining the characteristics described above varies with the characteristic being tested. For example, the general type of material buildup may be measured via resistivity and/or conductivity in conjunction with temperature. The chemical composition of the material on the road surface may be determined by spectrographic techniques, or by evaluation of EMR reflections. The percent of chemical(s) in a solution that has built up on a road surface may be determined by measuring the resistivity and/or conductivity of the collected material covering the sensor or by evaluation of EMR reflections. The freeze point of the solution may be determined by a software comparison, such as a table look-up, when the material components are known or determined by analysis when the material components are not known. The ambient temperature is measured via a thermometer or thermocouple which could be remote from the platform. The temperature of the solution/material buildup is measured by any known appropriate sensor means such as a thermometer, thermocouple or infrared sensor preferably mounted on the platform 12.

Alternatively, the freeze point of a solution can actually be determined by actually freezing the collected solution. The freeze point is determined by monitoring a property of the solution that indicates that the freezing temperature is reached, such as changes in electrical conductivity. This could eliminate the need for a look-up table.

The sensor platform 12 can be made of a thermoplastic material, or sensor flap material such as urethanes or teflon, and which preferably has the following characteristics:
impact/abrasion resistant;
low surface friction to maintain slipperiness to sheet the discharged material off of flap and sensor surface(s);

pliable and flexible temperature range of plus 150°–minus 40° F. degrees without melting or becoming brittle. Operating temperature of eighty degrees Fahrenheit (80° F.) to minus forty degrees Fahrenheit (−40° F.); and capable of using all sides for mounting of sensors and to be formed in such a way as to make sure that sensed material will be directed to the various surfaces as needed.

The sensor platform or flap 12, shown in FIG. 1, illustrates a variety of sensors mounted on or within it to illustrate the various mounting configurations for the purpose of making measurements or sensing certain characteristics of the material that has left the road surface as a result of turbulence or surface discharge behind the vehicle wheel.

The platform 12 is constructed to carry or have imbedded therein various sensors 18, 20, 22, and/or 24. These sensors, depending on their function, may protrude outside of or be recessed within the finished flap 12 so that they will be exposed to, or not exposed to, the material to be sensed, or will have access to the material to be sensed. As an alternative, the various sensors could be mounted with appropriate hardware onto an existing piece of flap material to achieve the same effect.

For example, sensors 18 and 20 may be a conductivity detector and/or a resistance temperature detector (RTD) or a thermocouple (TC) which senses the temperature of the material on the surface of the flap 12 and the presence of conductive solutions in the material such as potassium acetate, $CaCl_2$, NaCl, KCl or $MgCl_2$ in order to determine the type of material buildup. The lead wires from the conductivity cell and/or the RTD or TC are either embedded in or mounted behind the flap 12 for protection from abrasion and moisture.

Sensor 22 may be a sensor such as an RTD or TC mounted within an aperture 26 in the flap 12. The aperture 26 permits the passing air flow behind the wheel 14 to blow clear and thus ensure that new material continuously passes the sensor location. Other sensor locations in the aperture 26 are shown in dashed lines. The aperture 26 may also be used to direct flow of material past a sensor such as an EMR device.

The sensor 22A may alternatively be embedded in the flap 12 with the tip projecting to the front surface of the flap 12 to accurately measure the captured material temperature. Sensor 24 may be a RTD or TC mounted either behind the flap 12 or embedded within it so as to be representative of the ambient temperature of the flap 12. Alternative sensor locations may be incorporated into the sides or top of the flap 12 as indicated by the "S" thereon.

The flap 12 is preferably mechanically attached to the vehicle 10. The sensor flap 12 is designed to temporarily "catch" the discharge material from the vehicle's wheel 14. Alternatively, a separate sensor wheel 14A may be provided as shown in FIG. 3, for producing material discharge to be collected by a flap 12A which carries the sensors for making the measurements concerning the surface that the vehicle is riding over as well as detecting any buildup that might be on the surface—even after the buildup has left the surface. Sensor wheel 14A may also include embedded sensors thereon replacing the need for a flap 12A.

The incident spray material must not cling to the flap or plug any pass-through holes as new samples must periodically be measured/sensed. Therefore, proper material selection or cleansing methodology such as air flow is an important consideration in this first embodiment.

The sensors are connected to an in-cab display and control panel 28 via a cable 30 as shown in FIG. 2. The control panel 28 is capable of controlling, communicating with, and powering the sensors as well as interpreting sensor data and preferably includes display/input devices which can display information, accept outside input, store commands, and retrieve data. Alarm and control functions are also displayed on this panel. For example, interpreted data could include a freeze point prediction or alert notice for the measured solution and/or material.

Second Embodiment

A second embodiment of the surface condition sensing system in accordance with the invention is shown in FIGS. 4–8. The system in accordance with the second embodiment is specifically directed to determining the freezing temperature of a surface material. It includes an apparatus 38 that collects material from the road surface into a chamber, freezes it, determines the freezing temperature, communicates the data appropriately to a display/control console, and then thaws the material, empties the chamber, and prepares for the next measurement cycle. The apparatus 38 is mounted in a location on the platform 12 as disclosed above.

Figure 4:
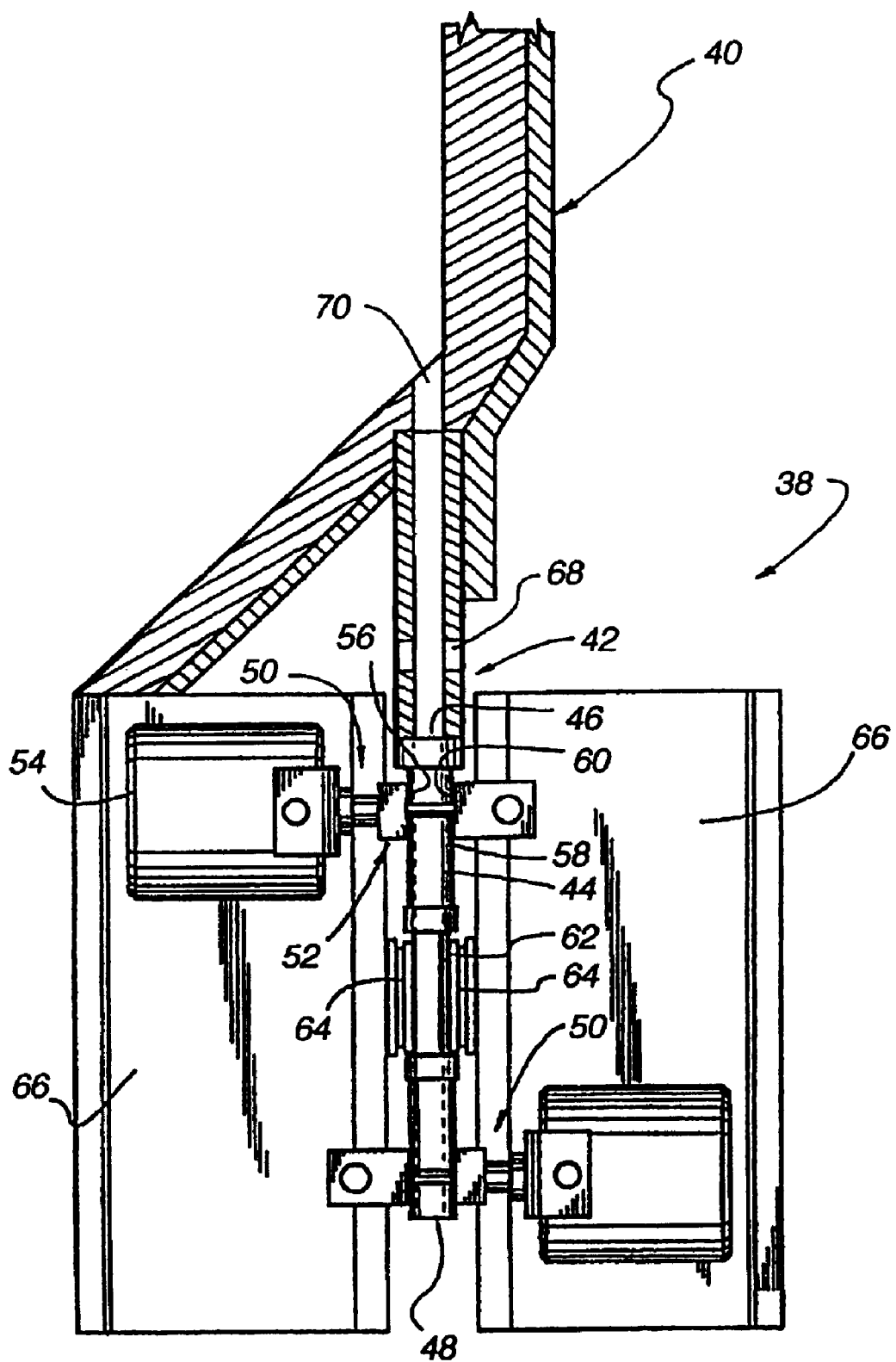
FIG. 4 is a partial side view of a second embodiment of a sensor platform for the travel surface material monitoring portion of the present invention.

The apparatus 38 associated with this system is seen in a side view in FIG. 4. The apparatus 38 comprises a support structure 40 made of any suitable material, for instance a laminate of a thermoplastic material and aluminum, and a capture and measurement portion 42 supported below and from the support structure 40. The capture portion 42 comprises an elongated chamber 44 having an open top end 46 and an open bottom end 48 generally having an elongated oval cross section. The open top end 46 is for receiving any surface material that collects above the top end 46 on the support structure 40.

The top end 46 and bottom end 48 of the chamber 44 are preferably made of a flexible material, such as plastic or rubber, which is preferably able to be selectively opened and pinched closed to allow material to flow in and out as desired. Selective opening and closing valve mechanisms 50 are mounted to the apparatus at the appropriate positions adjacent the upper and lower ends 46 and 48. When the bottom end 48 is closed and the top end 46 is open, collected material builds up in the chamber 44. When both ends are closed, the collected material is isolated. When both ends are open, the collected material is discharged from the lower end 48.

Each of the opening and closing mechanisms 50 includes a pinch valve 52 and a solenoid 54. The top and bottom ends 46, 48 of the chamber 44 are selectively opened and closed by pinch-valves 52. When the upper solenoid 54 is energized, it extends a shaft 55 outward and pushes a first surface 56, engaging a flexible portion 58 of the chamber 44 adjacent the upper open end 46, from one side and drives the flexible portion 58 towards the other side, which is in contact with a stationary second surface 60. The open top end 46 of the chamber is thus pinched closed between the first and second surfaces 56 and 60, causing a preferably impermeable seal to be formed at the top end of the chamber. The bottom end 48 of the chamber 44 is closed in a similar manner using a second solenoid operated pinch valve 52.

The chamber 44 has a central portion 62 of a predetermined length and width between the selective opening and closing mechanisms 50. This portion 62 preferably has an elongated oval cross section and is made of a conductive material, such as copper. The central portion 62 of the chamber 44 comprising a conductive material is thermally coupled to opposing plates of a thermoelectric heater/cooler 64 which controls the temperature of the central conductive chamber 44 using, for example, the well known Peltier effect. Although not shown in this Figure, it is to be understood that one or more temperature sensors are located in the chamber so as to sense the temperature of the chamber contents in order to determine the freeze temperature of the sample.

A heat sink 66 surrounds the chamber 44, preferably on all sides, along the length of the chamber 44 to facilitate the heating and cooling process as a result of the operation of the thermo-electric heater/cooler 64 and to preclude ice buildup on the exterior of the chamber 44. A liquid exiting aperture 68 is formed in the chamber 44 above the first surface 56 to allow any surface material draining into the liquid capture gap 70 to exit the chamber 44 when the flexible portion 58 of the chamber 44 is closed during operation of the thermoelectric heater/cooler 64. The draining liquid flows down over the heat sinks 66, preferably thereby beneficially affecting the heat transfer capabilities of the heat sinks 66.

Operation

The operation of this second apparatus may be either automatic or manual. In automatic operation, the apparatus operates continuously or at a predetermined cycle frequency as determined by the user, or it may be GPS/GIS triggered. In manual mode, the user actuates the apparatus each time road surface condition information is desired. This second embodiment of the road surface sensing system is used to collect surface material and accurately determine the freezing point of such material regardless of material composition.

The apparatus is positioned on the vehicle such that it is exposed to the spray of the surface material caused by the motion of the vehicle, as is schematically shown in FIG. 3. The apparatus may be positioned behind front or rear wheels, or may optionally include a separate wheel or scoop device to pick up material from the road surface, or, when the apparatus is used to analyze precipitation, a scoop device may be mounted on the upper portions of the vehicle 10, as suggested in FIG. 3, and directed upward to catch precipitation during vehicle motion.

Figure 5:
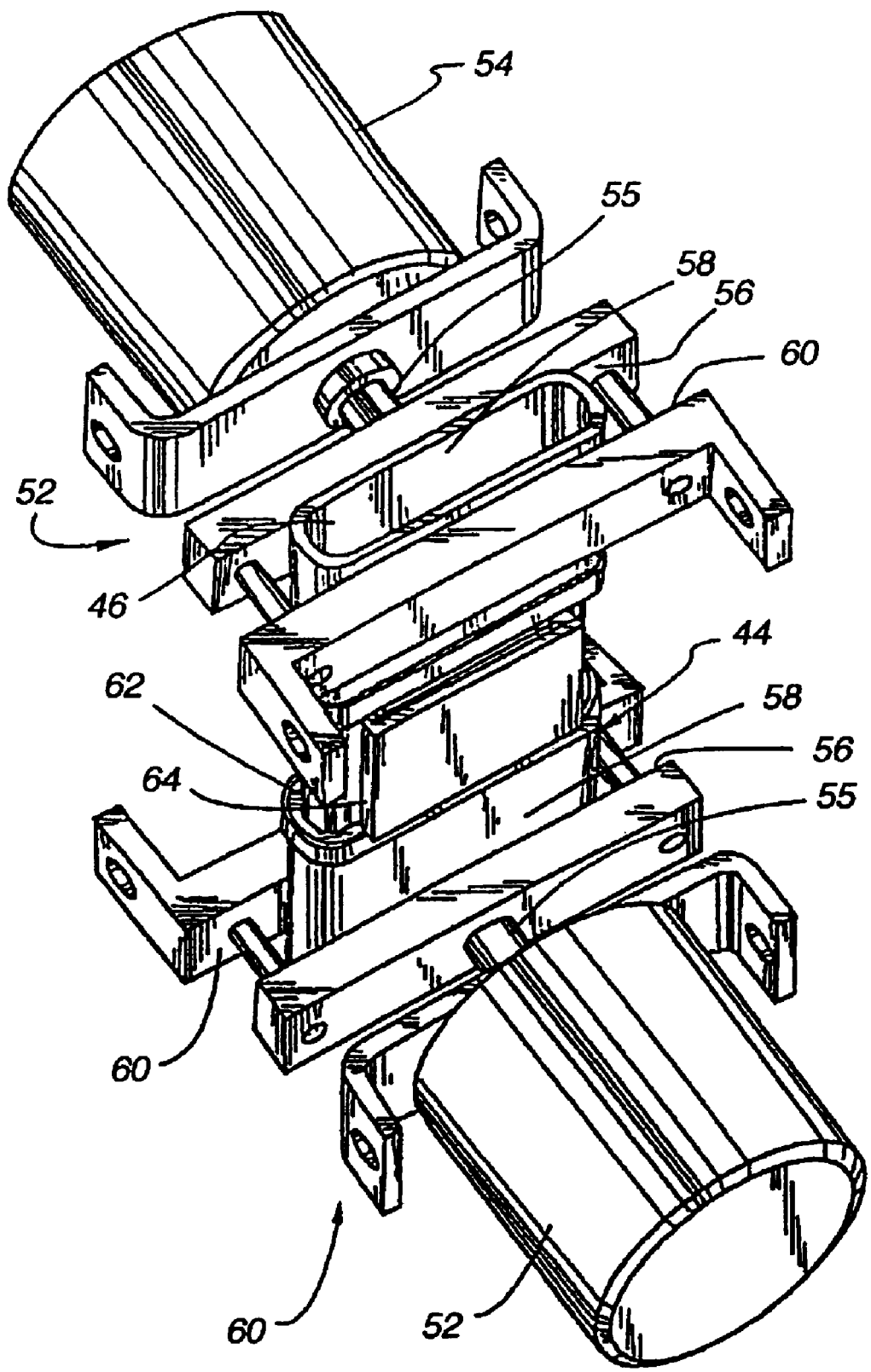
FIG. 5 is a perspective view of the second embodiment of the travel surface material monitoring portion of the present invention.

Referring now to the perspective view of the apparatus 42 in FIG. 5, when a measurement is to be taken, the bottom end 48 of the chamber 44 is closed. The surface material spray contacts the support structure 40, runs down the support structure 40 under the influence of gravity into the liquid capture gap 70. The surface material collects in the chamber 44 either for a programmable predetermined period of time, preferably about 5 to 10 seconds, or until the appropriate liquid level is obtained, at which time the top end 46 is closed by-closure of the upper pinch valve 52 to preclude entry of material that could contaminate the sample during measurement.

When a sufficient amount of surface material is collected in the chamber 44 and the upper pinch valve 52 is closed and the thermoelectric cooler 64 is activated to freeze the collected surface material. The electrical conductivity of the collected surface material is monitored in the chamber 44 during the cooling process to establish the freezing point of the surface material. This freezing point is communicated appropriately to the processor and display console 72, shown in FIG. 7.

After the freezing point is determined, the thermo-electric cooler 64 is activated to heat the conductive chamber portion 62 to melt the surface material. The bottom end 48 is then opened by de-energizing the lower pinch valve 52 to allow the surface material to exit the chamber 44. The process can then be repeated to obtain a new reading.

Figure 6:
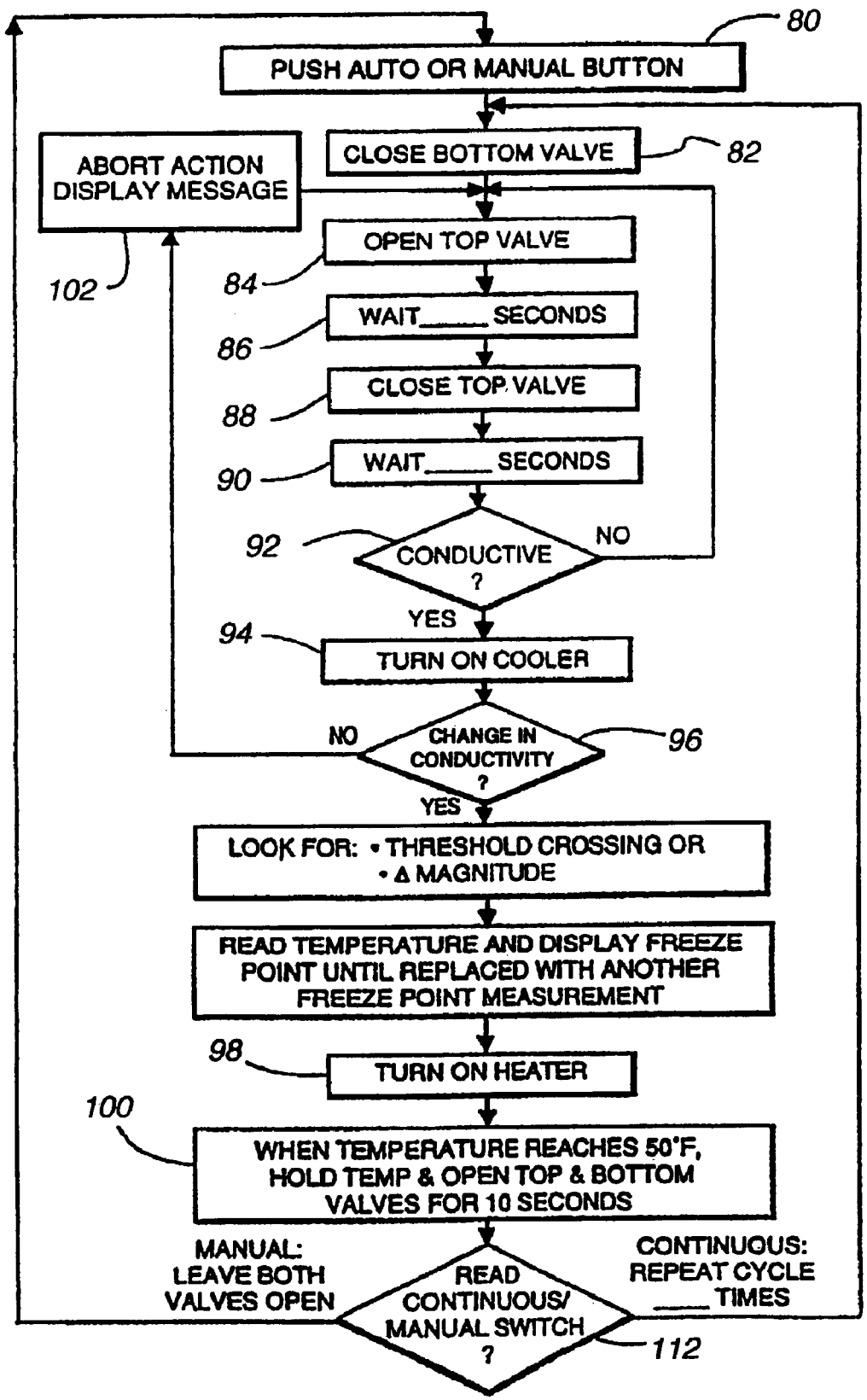
FIG. 6 is a control block diagram of the second embodiment of the travel surface material monitoring portion of the present invention.

More particularly, referring to FIG. 6, and to FIG. 7, automatic operation of the apparatus in accordance with this embodiment of the invention proceeds as follows for determination of freeze point by measuring the liquid to solid phase transition temperature. As previously mentioned, the freeze point may also be determined by sensing the solid to liquid phase transition during thaw. In this latter situation, the sequence described below will be somewhat modified. The user places the automatic/manual selector switch 80 in the automatic position. When the switch 80 is placed in the automatic position, a signal 82 is sent to close the bottom valve and a signal 84 is provided to de-energize the upper solenoid valve 52 so that collected material may flow into the chamber 44. The control system then pauses for a predetermined amount of time, such as ten seconds, in block 86. At the expiration of this wait period, a signal 88 is sent to close the upper valve 52 in order to isolate the sensing portion 62 of the chamber 44. Preferably, another programmable wait period 90 of a predetermined length of time is conducted after which the processor tests whether the contents of the central portion 62 of the chamber 44 is conductive. This test of conductivity 92 is necessary in order to sense whether there is sufficient material collected in the chamber. If the material collected in the chamber is conductive, a signal 94 is sent to turn on the thermo-electric heater/cooler 64 in the cooling mode. Conductivity is continually monitored in block 96 to determine a significant change in conductivity, as the material in the central portion 62 of the chamber 44 is cooled, which indicates that the freezing threshold has been reached. This threshold is normally indicated by a substantial change in magnitude of the conductivity signal. If the threshold of freezing is detected in block 96, the processor then sends a signal 98 to turn on the heater until it reaches a temperature substantially greater than the threshold, for example, about 50° Fahrenheit. When this temperature is reached, a control signal 100 is sent to de-energize both upper and lower solenoid valves 52 for a programmable period of time sufficient to permit the collected material to drain from the chamber 44, for example, ten seconds. On the other hand, if, in block 96, no threshold crossing was sensed, an abort action display message signal 102 is displayed and the automatic process steps 80 through 96 are repeated.

Figure 7:
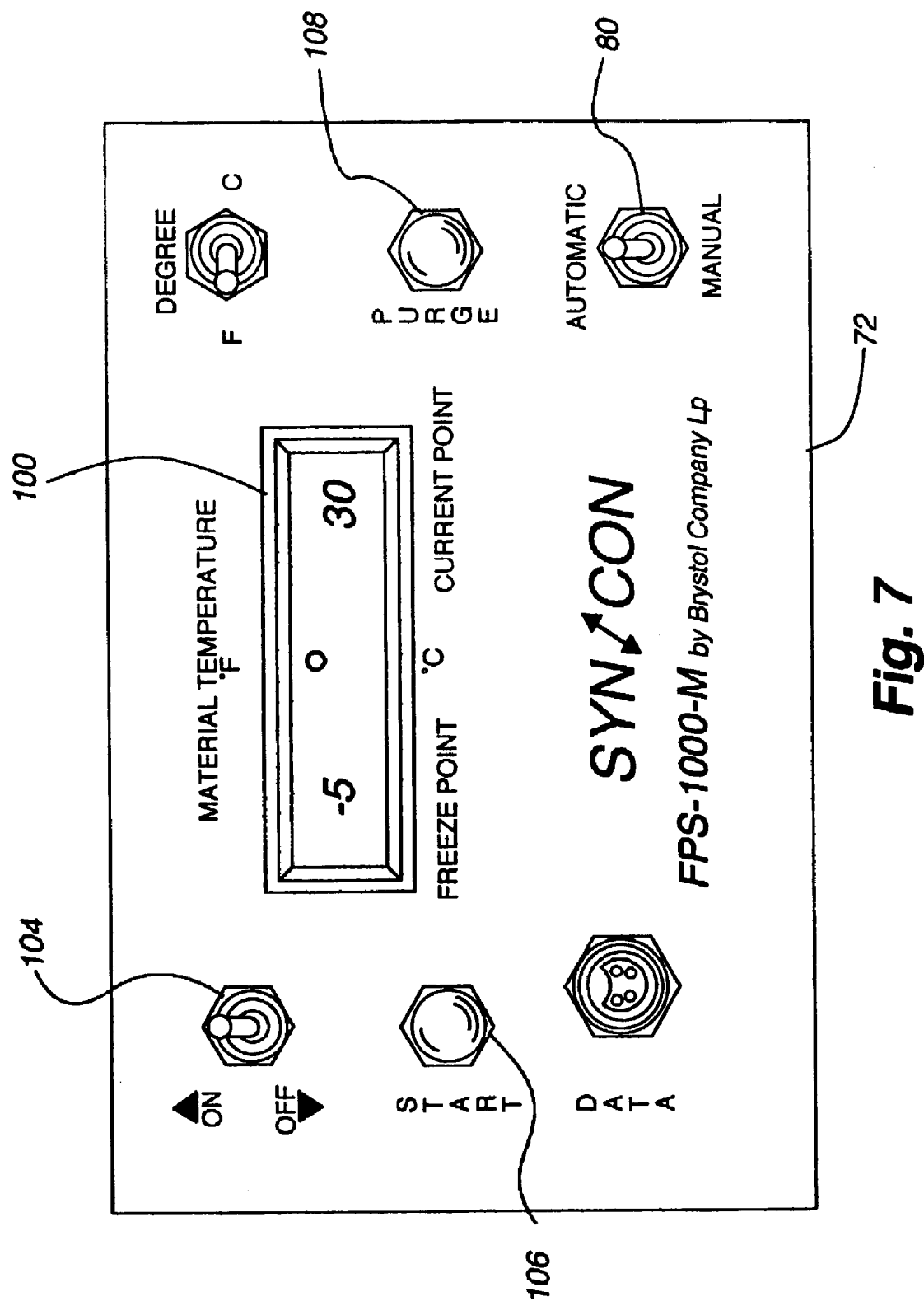
FIG. 7 is front view of the display panel in the second embodiment of the surface monitoring portion of the present invention.

Referring now to FIG. 7, the display console includes an on/off switch 104, a start switch 106, a purge switch 108, and a display 110. Manual operation or automatic operation is selected by switch 80. When the manual operation is selected, the purge switch 108 may be pressed by the operator. This de-energizes both inlet and outlet valves 52, allowing any materials contained in the chamber 44 to be discharged. The start switch 106 is pressed and the automatic or manual control process shown in the flow chart in FIG. 6 is performed from block 82 through block 100. After the chamber temperature has reached 50° in block 100, the processor determines in block 112 whether switch 80 is in the automatic or manual position. If in the manual position, a signal is sent to leave both valves 52 open and await further manual instructions. If switch 80 is in the automatic position, however, the process is automatically directed to block 82 in which the bottom valve 52 is closed and the sample collection and evaluation process is repeated a programmable number of times.

Figure 8:
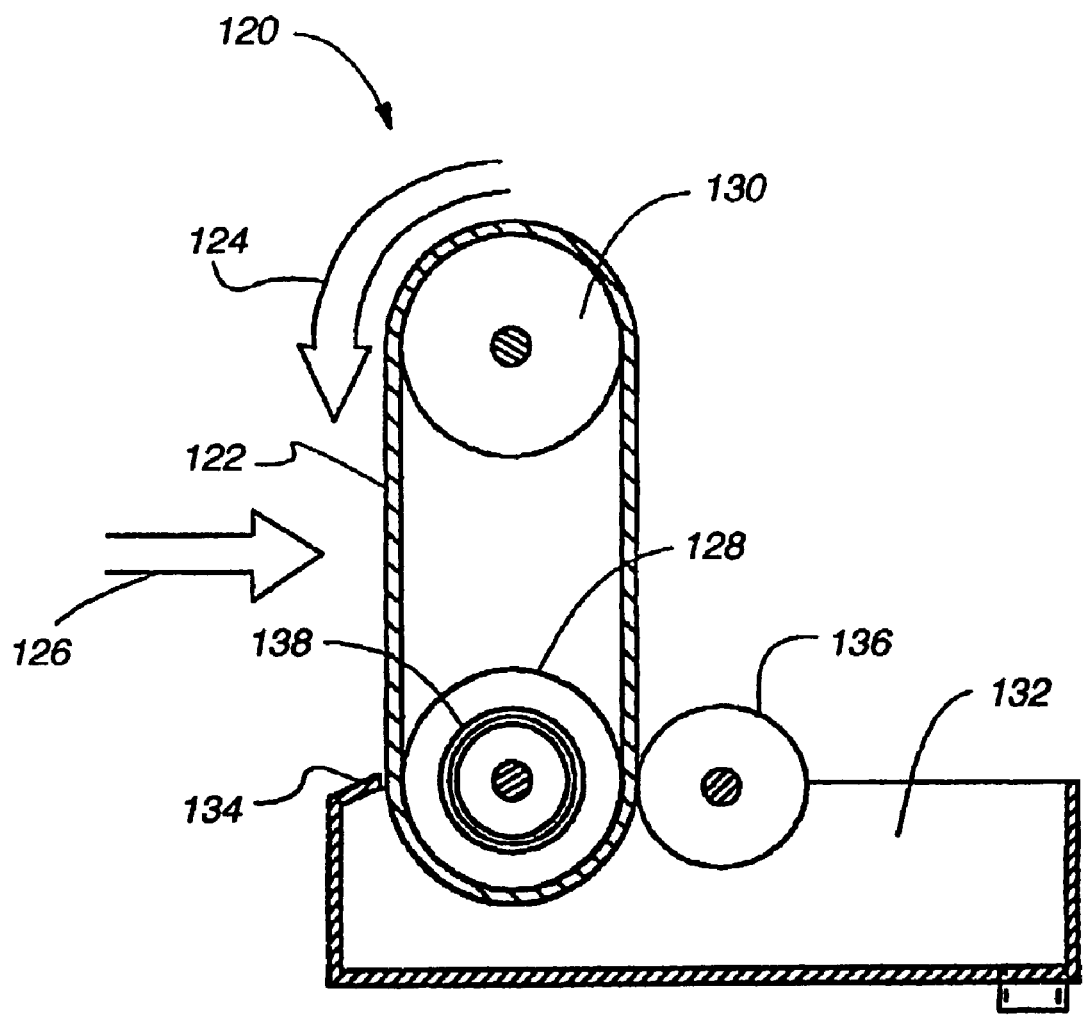
FIG. 8 is a schematic side view of an alternative collection apparatus of a vehicle travel surface monitoring portion of the system in accordance with the present invention.

Referring now to FIG. 8, the apparatus in accordance with the second embodiment may be modified to include a collection apparatus 120 that incorporates an endless belt 122. In operation, the endless belt 122 moves in the direction of the arrow 124. Road debris thrown up by the vehicle moves and impinges on belt 122 in the direction shown by arrow 126. The lower pulley 128 is preferably either hydraulic motor driven or electrically driven. The upper pulley 130 is preferably spring biased away from the motor driven pulley 128 to maintain tension on the belt 122. A collection hopper 132 is positioned below the motor driven pulley 128 and discharges into the open upper end 46 of the collection chamber 44 above described. A scraper 134 is positioned adjacent the front facing portion of the belt 122 before the belt 122 enters the hopper 132 so that as it enters the hopper 132, leaves and other solid debris may be scraped from the belt 122.

A pinch idler pulley 136 is mounted adjacent the motor driven pulley 128. As the belt moves around the pulleys counterclockwise as shown in FIG. 8, liquid picked up from the road is "squeegeed" into the hopper 132 as the belt 122 passes between idler pulley 136 and driven pulley 128. A spring-loaded clutch 138 may also be provided on the motor driven pulley so that the collection apparatus 120 does not operate while the central portion 62 of the collection chamber 44 is isolated.

Third Embodiment

A block diagram of a third embodiment of the vehicle travel surface material sensing portion of the system in accordance with the present invention is illustrated in FIG. 9. This third embodiment is a completely remote sensing apparatus which is mounted on the vehicle. This system 200 includes at least one electromagnetic radiation transceiver 202 which preferably is an ultra-wide band (UWB) impulse radar. A very short electromagnetic impulse is propagated from transceiver 202 and echoes that reflect from the road surface 204 are evaluated. These reflected signals are sent to a depth processor 206, a density processor 208, and at least a chemical composition processor 210. The EMR reflected pulse or pulses may be utilized directly by the depth processor 206 to determine the depth of any surface layer of material on the roadway. However, the density processor, and composition processors 208 and 210 rely also on input from a database 212 to determine, by comparison to peak height or phase shift of the reflected signal versus the incident signal, an output which is unique to a particular chemical composition and density. Comparing these outputs to the database content produces or can result in quantitative density and composition information which is, in turn, fed via lines 214 to computer 216 along with depth information 218. This information is, in turn utilized by the computer 216 in conjunction with the database 212 to determine the freeze point temperature of the particular composition of the material on the vehicle travel surface. The freeze point determination result is then processed along with the depth 218 information in the computer 216 to provide information necessary to determine what additional chemicals, both type and amount, need to be deposited on the road surface in order to minimize the hazardous conditions and provide the results on the display 220. In addition, the computer 216 may provide a direct output to a control device for automatically dispensing the appropriate amounts of chemicals to the road surface as the vehicle 10 drives along.

A temperature sensor such as an infrared transceiver 222 is also mounted on the vehicle and is directed toward the road surface. The transceiver 222 provides an output to a road temperature processor 224 which in turn also feeds an output to the computer 216 indicative of the actual surface temperature of the road or, if covering material such as snow or water are present, the actual temperature of the material on the road surface.

The apparatus 200, in accordance with the third embodiment of the present invention, may be compactly designed for unitary installation in the cab of a road maintenance vehicle, such as a salt truck, with the display 220 and any input device such as a voice recognition device or keyboard 226 integrated into the dashboard of the vehicle. The driver can then input to the computer 216 desired deicing concentrations or other desired input information. This inputting may also be remotely triggered automatically from a location remote from the vehicle or by the vehicle arriving at a predetermined as evidenced by GPS/GIS coordinate data under software control. The computer 216 then can compare the actual composition and status of the material actually on the road and either display or automatically control the dispensing of additional chemicals to the road surface.

The temperature sensor, such as an infrared transceiver 222 described above, measures only the temperature of whatever material is on the surface. It does not measure the roadway temperature unless the surface is dry. Consequently, the apparatus 200 may also include a travel surface temperature sensor and/or a subsurface temperature sensor 228 connected to a surface and subsurface temperature processor 230 which, in turn, provides a surface and/or a subsurface temperature signal to the computer 216. The surface/subsurface sensor 228 may be a short range ground penetrating radar transceiver unit which is calibrated for determining road surface temperature subsurface temperature at a depth of preferably about 12–18 inches. This subsurface temperature information can then be used by the computer 216 to estimate the heat capacity of the road bed and thus predict the rate of change of surface temperature for a given atmospheric set of conditions plus calculate application rates for various surface conditioning materials, in particular, those materials which may be readily available on the vehicle or available on a different vehicle which may be expeditiously rerouted to the appropriate location.

Weather Monitoring Portion

Figure 10:
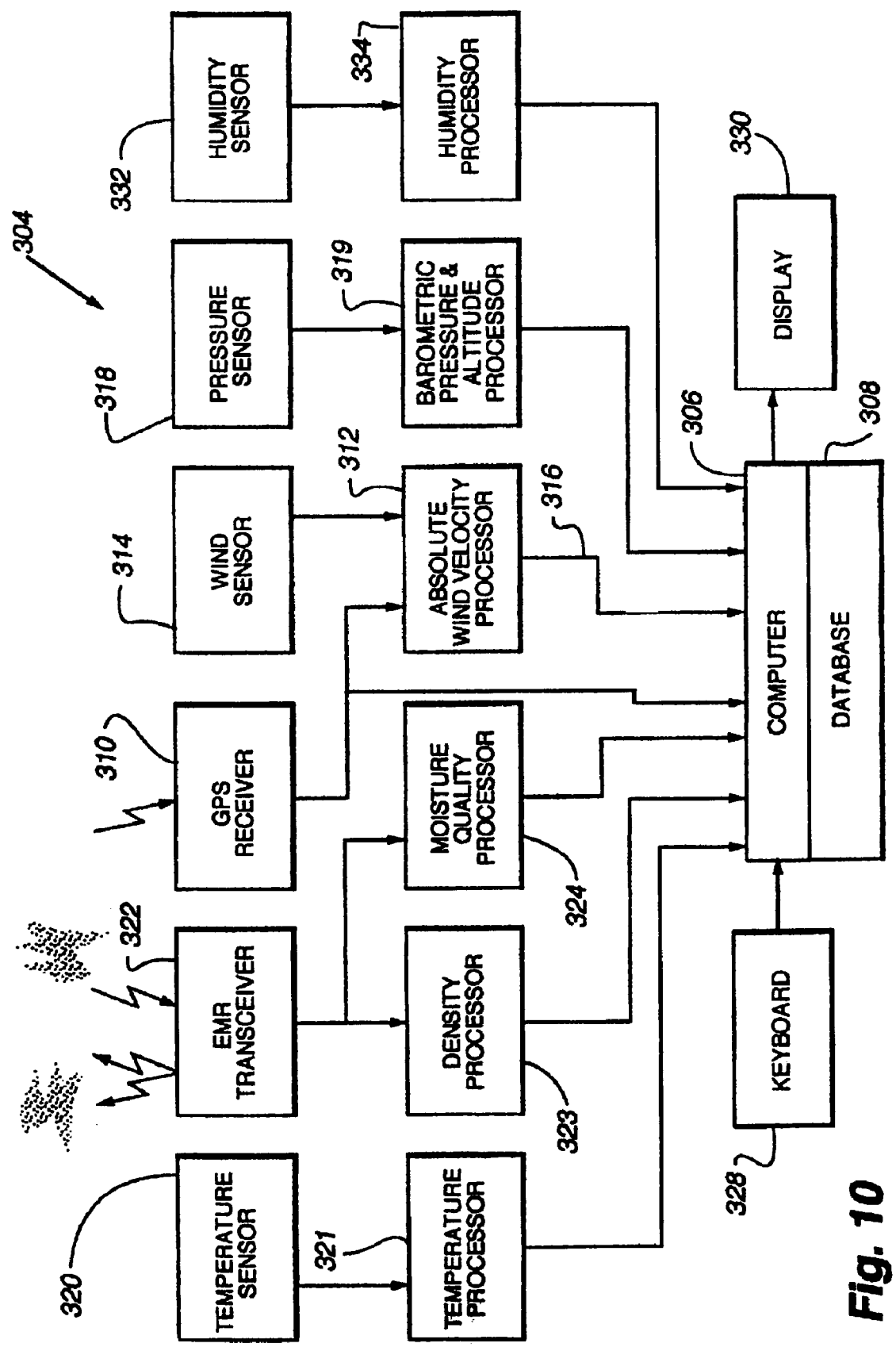
FIG. 10 is a block diagram of a remote sensing embodiment of the weather monitoring portion of the system in accordance with the present invention which may be mounted on a vehicle or at a stationary location.

A preferred embodiment of the weather monitoring portion 304 of the system 300 is shown in block diagram form in FIG. 10. The weather monitoring portion 304 has a Global Positioning System (GPS) receiver 310 mounted in the vehicle 10. The GPS receiver 310 constantly monitors a plurality of geo-synchronous orbiting satellite signals and can receive typically 12 simultaneous position signals to accurately triangulate the vehicle's position at any moment and provide accurate coordinates of the vehicle 10 to the computer as well as generate and provide a velocity signal (both speed and direction) to the central computer 306 and to an absolute wind speed and direction processor 312.

The wind speed and direction processor 312 also receives an input from wind speed and direction sensor 314 which is preferably mounted in an exterior location on the vehicle 10 such as on the roof of the cab of the vehicle 10. The wind sensor 314 may be any suitable wind speed and direction sensor, however, a Model 425 Ultrasonic Wind Sensor by Handar International of Arlington Va. is presently preferred. This wind sensor 314 uses ultrasound to determine horizontal wind speed and direction based on ultrasonic transit time between three spaced transducers spaced 120° apart. This sensor is described in detail in U.S. Pat. No. 5,343,744. The sensor 314 has both analog and digital outputs.

The wind speed and direction processor 312 essentially converts the vehicular mounted wind sensor output signal to a vector having both magnitude and direction, and then subtracts the vehicle motion vector (speed and direction) generated by the GPS receiver 310 to yield absolute wind speed and direction independent of the vehicle motion, i.e., absolute wind velocity. The absolute wind velocity signal is then fed on line 316 from the wind speed and direction processor 312 to the computer 306 where it is utilized, for example, in conjunction with a wind chill lookup table in the database 308 to determine a correction factor to be applied to the freeze point determination for the surface material information as provided by the computer 216 described above. This may be necessary, for example, in those locations where the roadway surface may be subject to high winds. In addition, the historical data provided in the database 308 may be used to indicate to the central computer 306 that the particular location, as determined by the GPS receiver in conjunction with geographical information system data stored in the database 308, historically has required a greater or lesser amount of treatment than would be otherwise be indicated.

The weather monitoring portion 304 may be stationary or vehicle mounted and preferably also includes a pressure sensor 318 and pressure processor 319 for determining barometric pressure and altitude, an air temperature sensor 320 and temperature processor 321, and an EMR transceiver 322 which is preferably directable skyward or directable toward any moisture source. The transceiver 322 preferably utilizes a wide band short range radar or laser based range finder to determine the presence or absence of precipitation near the vehicle 10. The transceiver 322 feeds a moisture quality processor 324 which determines at least one characteristic of the sensed precipitation such as moisture content and precipitation rate. For example, the intensity of reflections detected by the transceiver 322 provides an indication of the precipitation rate and/or moisture content. In addition, the transceiver 322 also feeds a density processor 323. The output of the density processor 323 is connected with the computer 306.

The transceiver output is fed to the processor 324 where the magnitude and character of reflections are analyzed. By evaluating the character of reflections received, the differential between the precipitation state in the air (rain, snow, wet snow, dry snow, sleet etc.) and the freeze point of the precipitating water or ice or combination, once it is deposited on the travel surface, can be more accurately determined. This information is then used by the computer 306 to compensate for and optimize the computation of additional material needed to be deposited on the vehicle travel surface as calculated by the surface condition monitoring portion 302.

A humidity sensor 332 may also be provided which is coupled to a humidity processor 334. The humidity processor 334 also receives an air temperature input from the air temperature sensor 320 which, when combined with the humidity sensor output, determines the amount of moisture in the air that has not coalesced into precipitation and determine, in essence, the dewpoint of the air. The humidity processor output is fed to the computer 306 in order to predict the potential for increase or decrease in the amount of or quality of the precipitation accumulating on the travel surface.

Figure 11A:
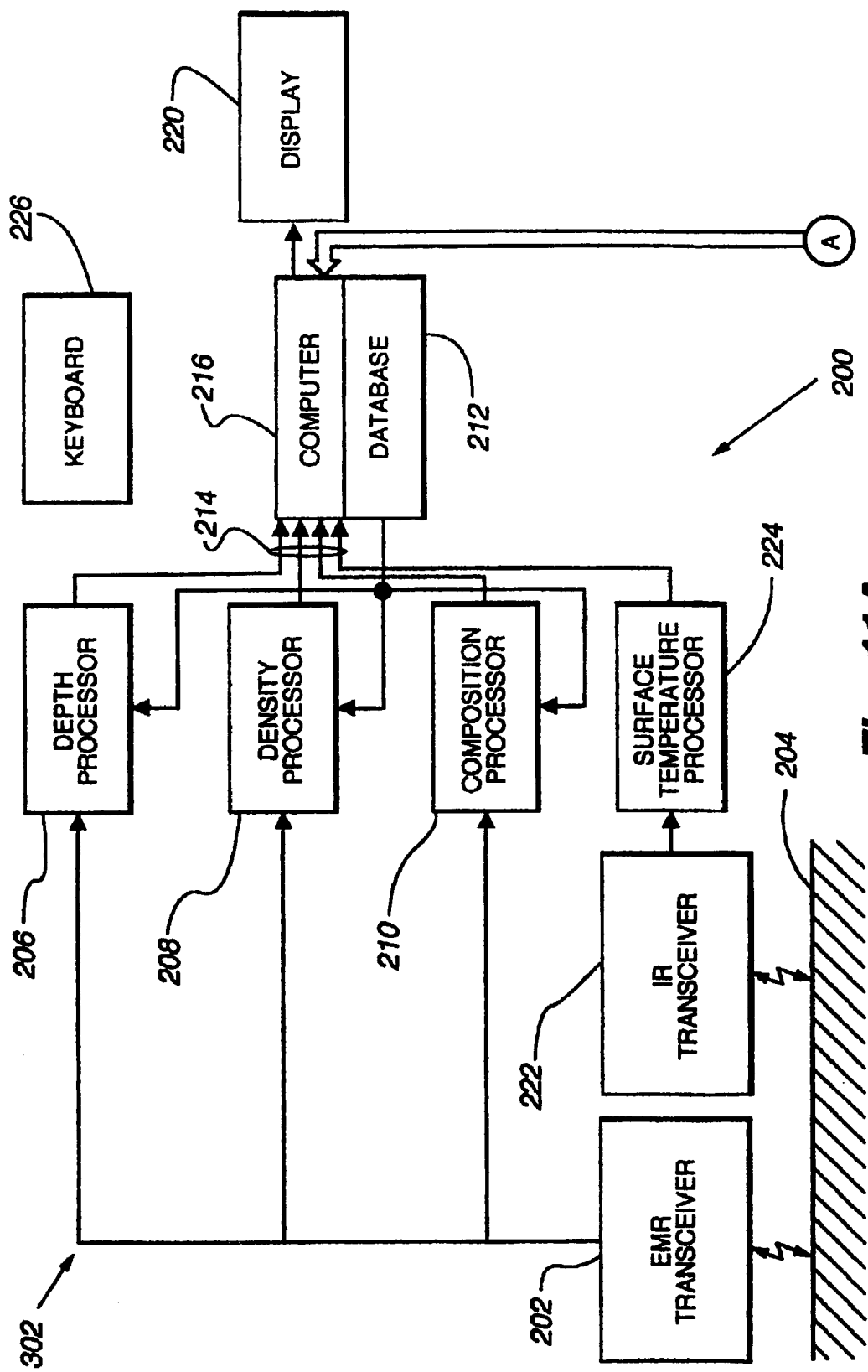
FIGS. 11A and 11B are an overall block diagram of the system in accordance with the present invention.
Figure 11B:
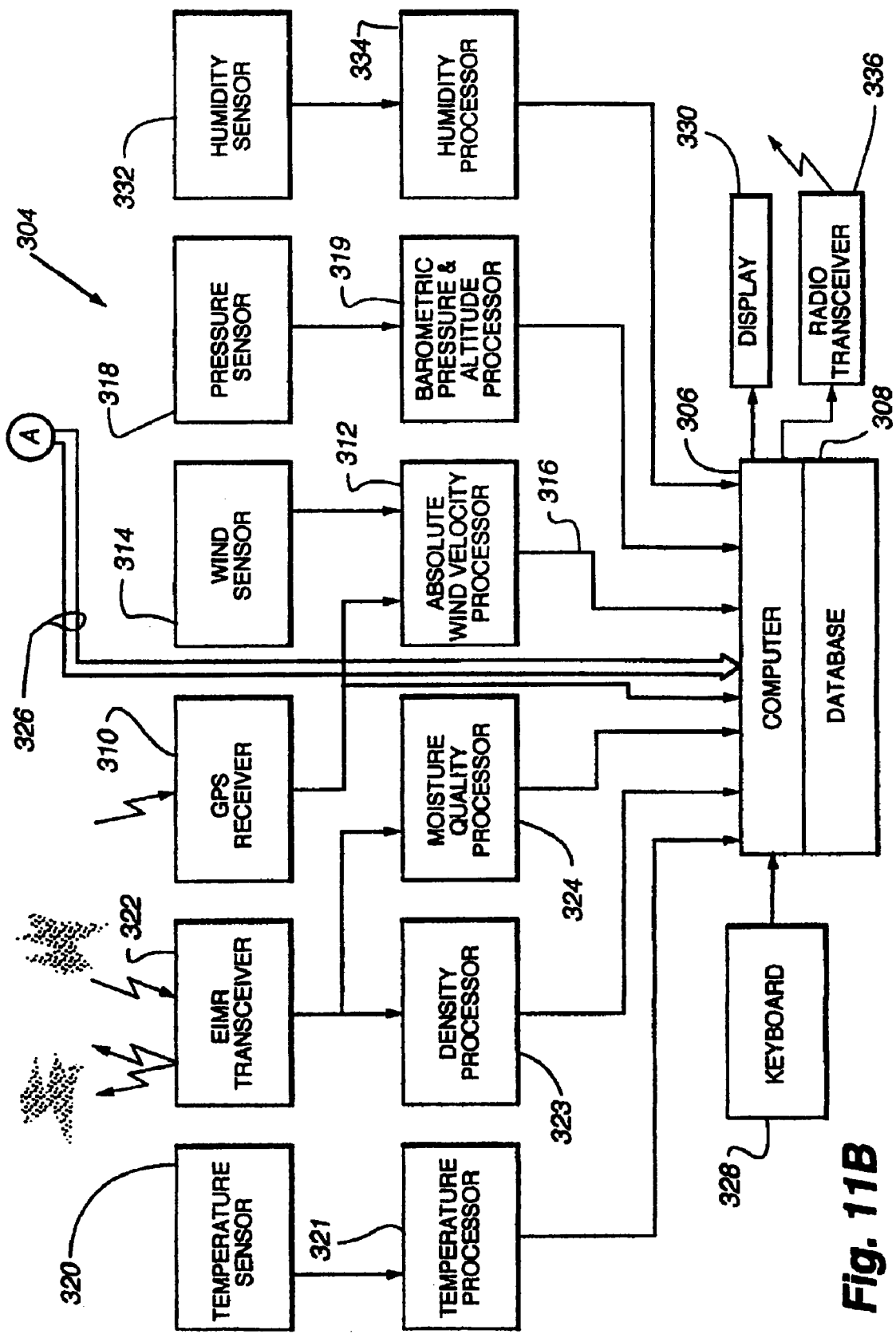

Referring now to FIG. 11, the overall system 300 can utilize two separate computers 216 and 306 and databases 212 and 308 and/or a communication link between the computers and databases, but only one computer and database is needed. These components preferably communicate, in this example, via bus 326. Either one of the computers 216 or 306 may be programmed to operate or function as a master control and the other as a slave to the overall program of the master control. It should be understood that these computer and database functions described herein may just as easily be combined and provided by a single computer and database to which each of the sensors and signal processors connects. Therefore, this combined configuration is to be understood and will not be illustrated as it is essentially redundant to what has already been described.

The system 300 may preferably comprise two separate stand alone systems, portion 302 consisting essentially of the surface material condition monitoring system 200 and the vehicle mounted weather monitoring portion 304. As such, the weather monitoring portion 304 may have its own separate input/output devices such as a keyboard 328 and a display 330. Alternatively, keyboard 226 and display 220 may be utilized to provide user control and display functions for both portions 302 and 304 via bus 326. In addition, the system 300 may include a radio transceiver 336 connected to the computer 306 to provide two way remote communications, reporting and control functions to and from a remote command center (not shown) or computer 216.

Figure 12A:
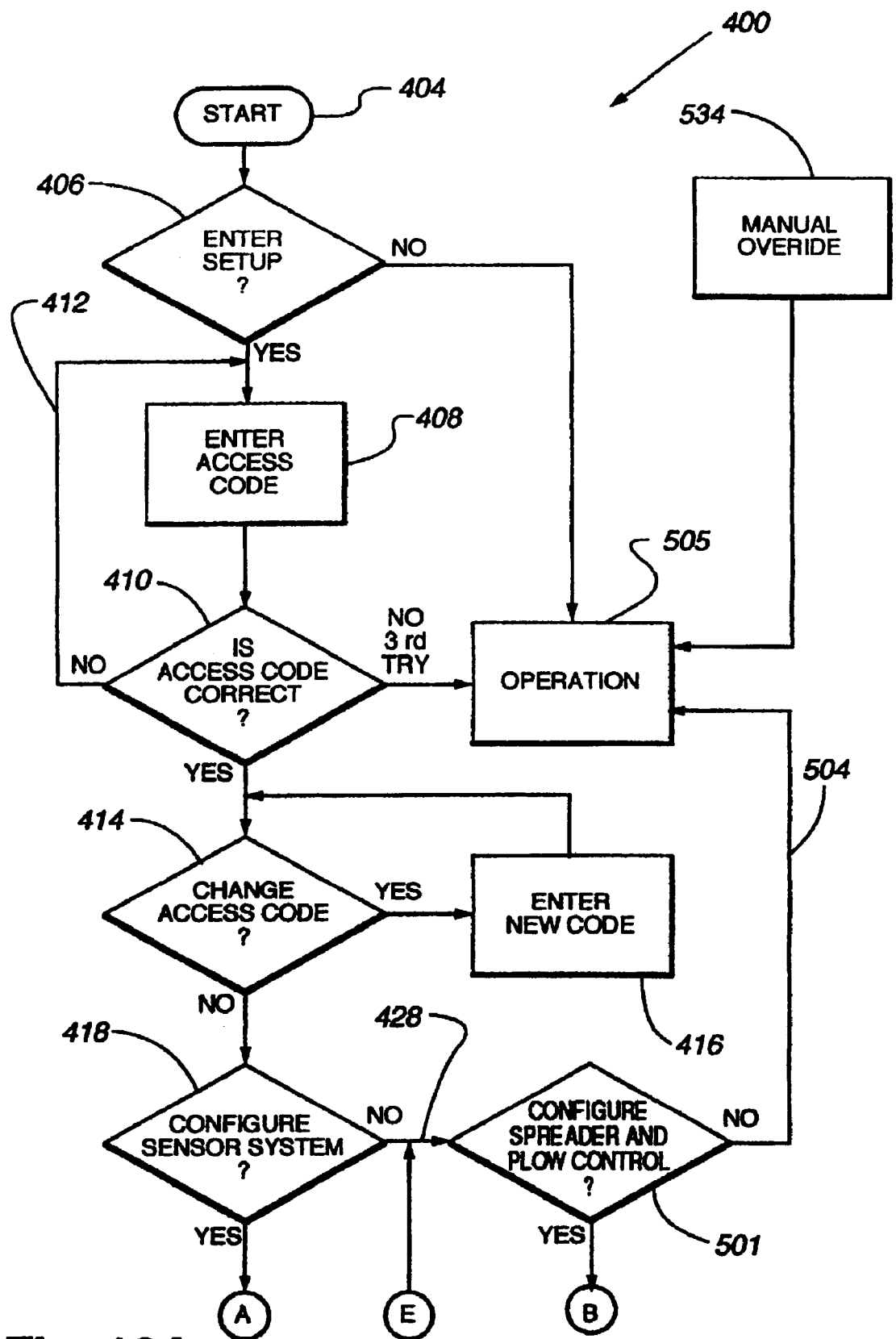
FIGS. 12A–E are overall software block diagrams of the software decision flow block in accordance with the present invention.
Figure 12B:
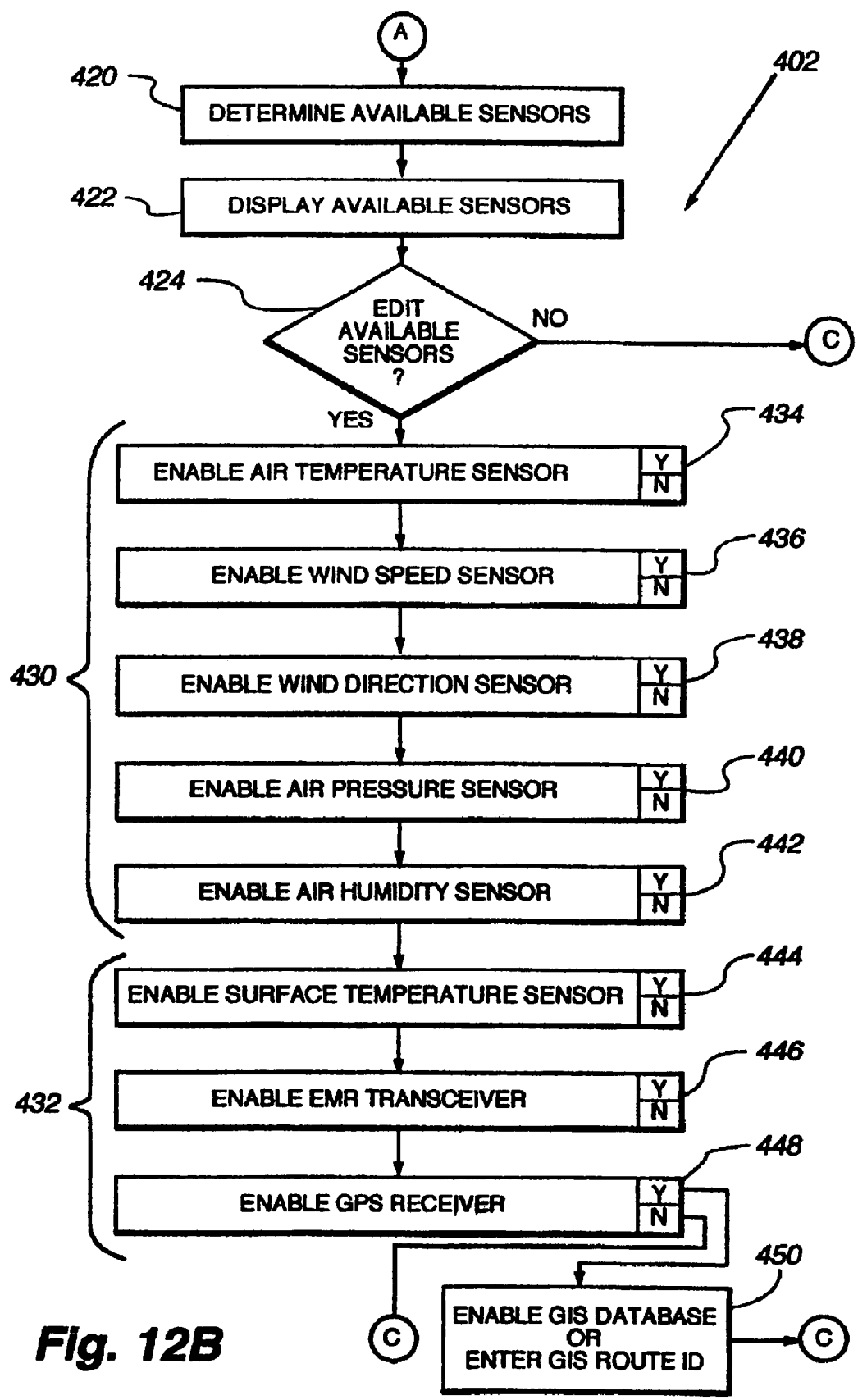
Figure 12C:
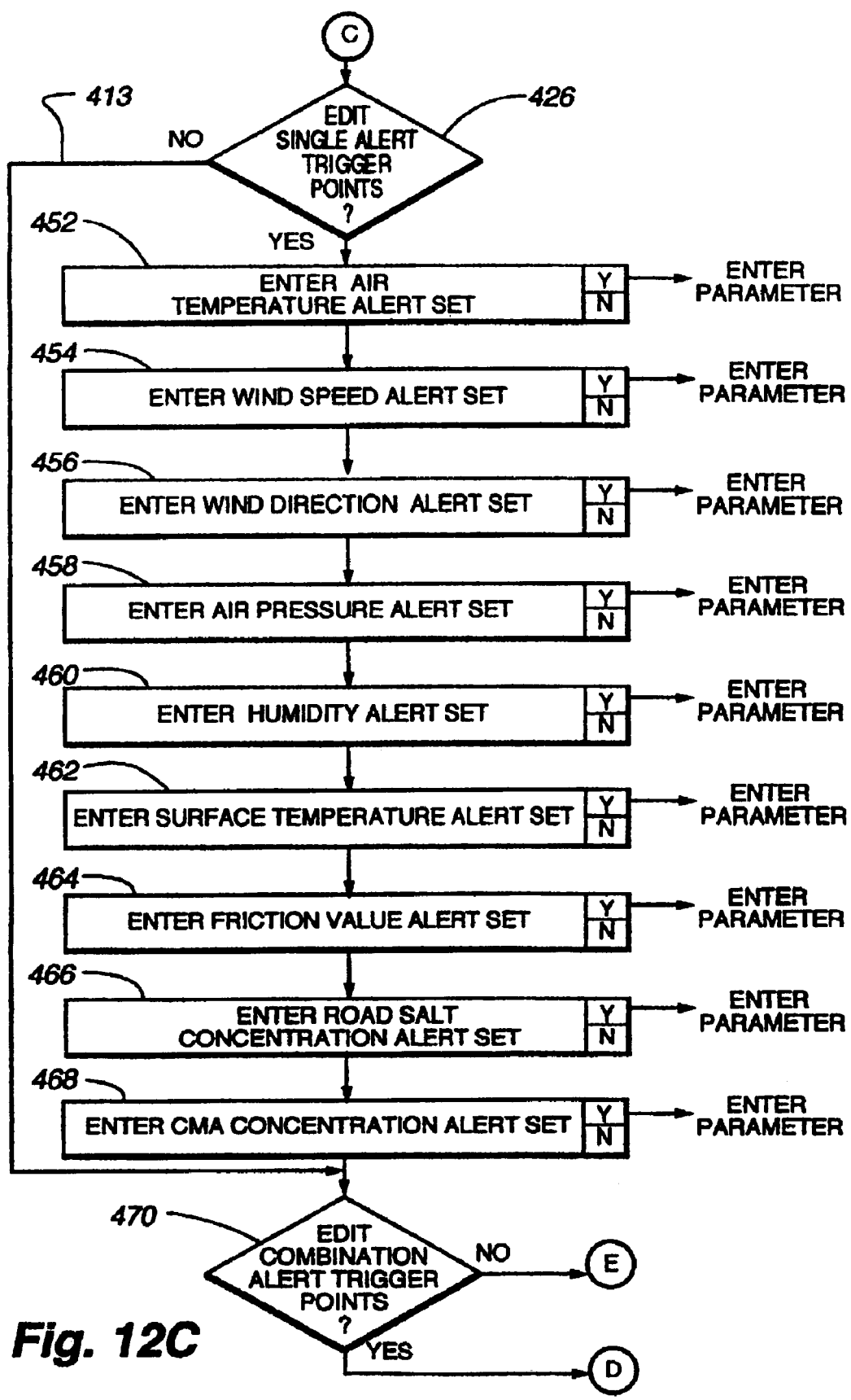
Figure 12D:
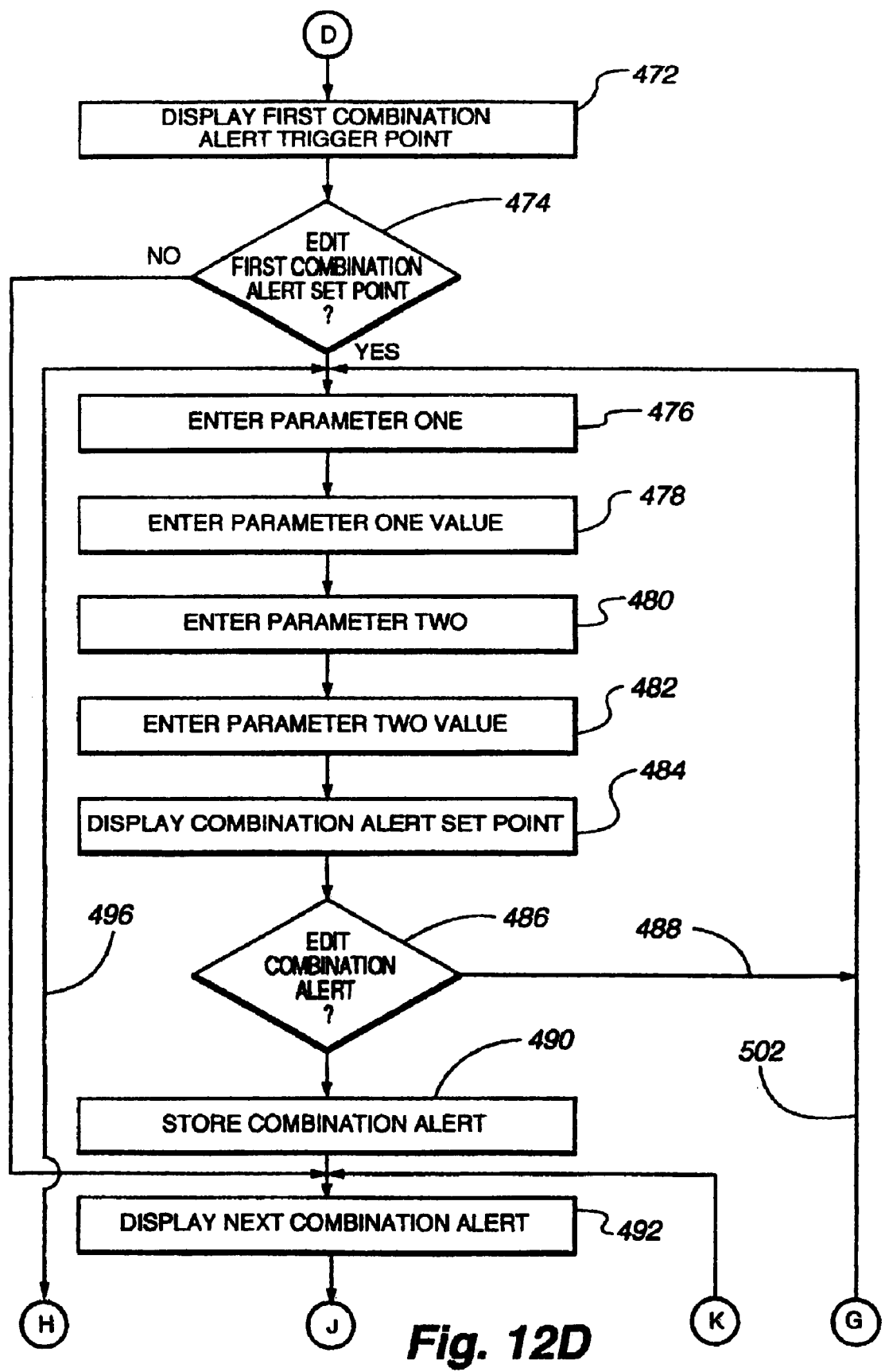
Figure 12E:
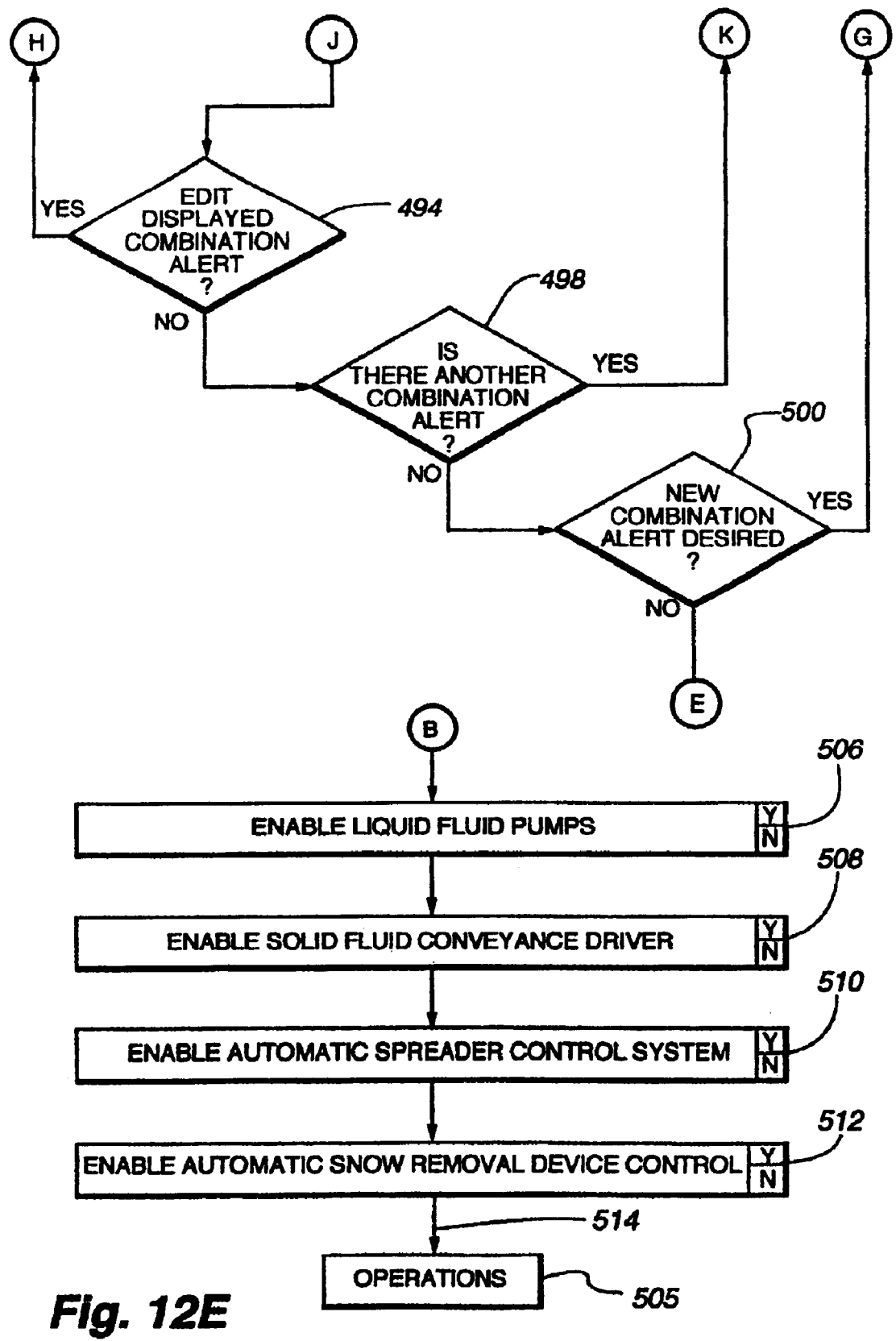
Figure 13:
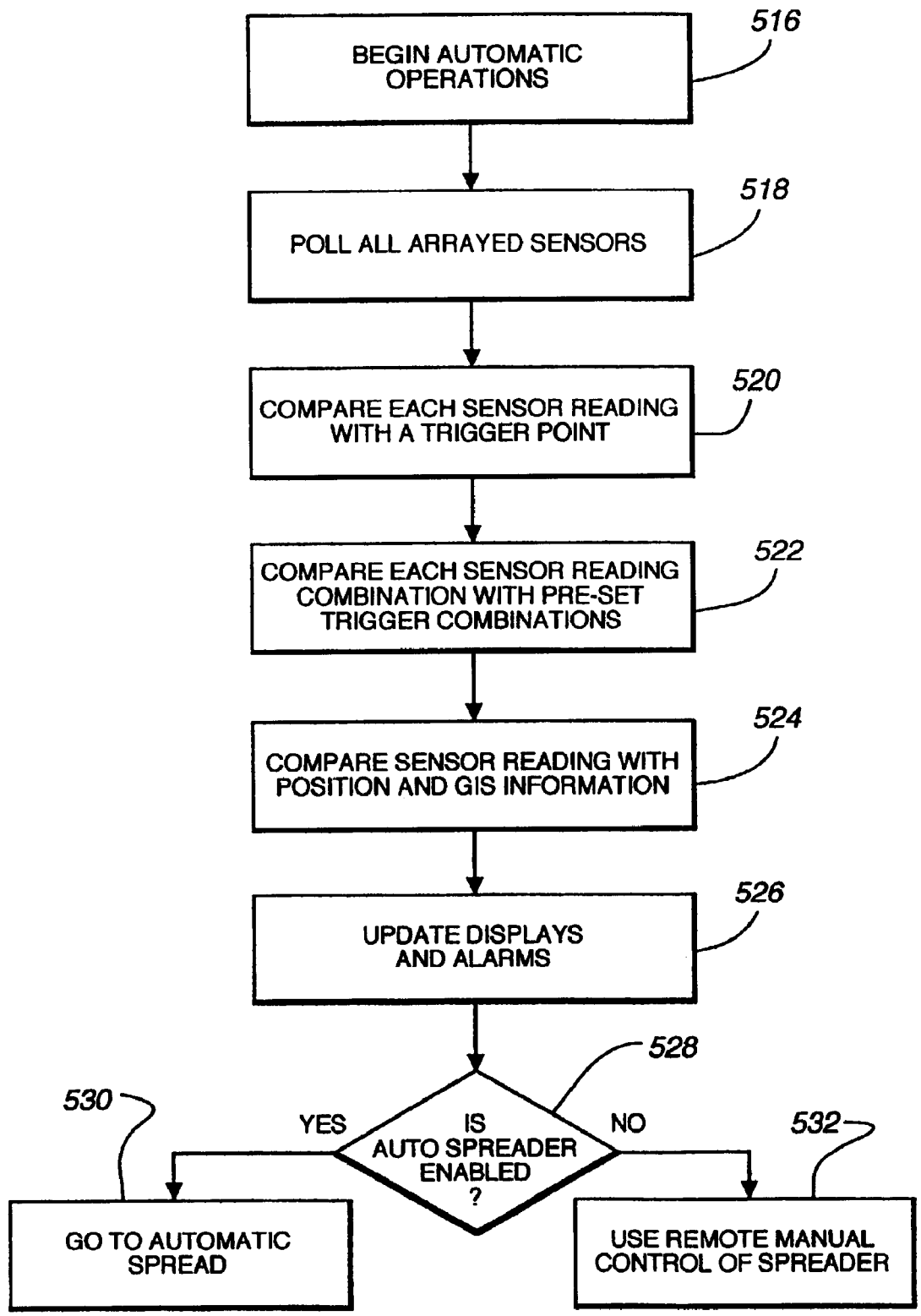
FIG. 13 is a block diagram of the automatic system operation block in accordance with the present invention.

A software decision flow block diagram 400 of one embodiment of the overall system 300 in accordance with the present invention is provided in FIGS. 12 and 13. It is to be understood that this representation is but one way of utilizing the information provided by the surface material condition monitoring portion and the weather condition monitoring portion. The system provides, via suitable dispensing controls or recommendations to the vehicle operator via the display(s), an optimized treatment plan for the vehicle travel surface such as a road or runway surface depending on actual field conditions.

Generally, the user may choose to set-up both the vehicle's sensor system, including enabling the sensors and appointing alert set points, and the vehicle's automatic spreader and plow, or to proceed to the systems operations block 505, where the system is either set for automatic operations or is by-passed for manual use.

The user (driver) enters the vehicle and turns on the ignition. The system 300 powers up and begins the sequence in operation 404, as shown in FIG. 12A. After the system is started the user is queried in operation 406 if entry into set-up mode is desired. If yes, control transfers to operation 408 which requires the user to enter a pre-programmed access code. When a code is entered, control then transfers to operation 410 where the entire code is compared to a previously stored code. If the user unsuccessfully enters the correct access code, control transfers via line 412 back to the query block 408. The user is given three tries at entering the proper access code. After the third unsuccessful attempt to enter the proper access code, the user is automatically transferred to the operations block 505. It is also contemplated that a third failed attempt to enter the access code could result in the automatic shut down of the software decision flow block and potentially the vehicle ignition is automatically turned off, until it is re-set by the user's supervisor.

If the proper code is successfully entered, control transfers to operation 414 where the user is queried as to whether the current access code should be changed. An affirmative answer transfers control to operation 416 which requires the user to enter a new code. Once the new code has been entered, control transfers back to operation 414, affording the user the opportunity to continue changing the new code until the user is satisfied.

Upon entering the new code, or if the user declines to change the old code, the user is queried in operation 418 whether the sensor systems associated with the vehicle need to be configured. A negative response to query operation 418 will bypass the sensor system setup operational blocks and transfer control via line 428, to operation 501 to configure automatic spreader and plow control.

A positive response to query operation 418 transfers control to operation 420 in FIG. 12B. Here, the user can configure or reconfigure the sensor system. The available sensors may either be entered manually by the user, or the program can automatically scan the sensor hook-ups and communication links to determine the available system sensors 420. Once the available sensors are determined, a list of each sensor is displayed in block 422. The user is then queried in operation 424 as to whether to edit the available sensors. If the user does not wish to edit the available sensors, the program control transfers to operation 426 in FIG. 12C, where the user is asked whether any single alert trigger points are to be edited.

If the user does want to edit the available sensors in operation 424 control transfers the user to the first of the enabling block queries 434. By following the programs progression, the user will be allowed to enable any available sensor installed on the vehicle.

Each sensor enable operation block corresponds to either one of the environmental monitoring sensors 430 or to one of the remote surface condition monitoring sensors 432. For example, environmental monitoring system sensors may include: air temperature sensor 434, wind speed sensor 436, wind direction sensor 438, air pressure sensor 440 and air humidity sensor 442. The remote surface condition monitoring system sensors may include: surface temperature sensor 444, EMR transceiver 446, and GPS receiver 448.

The user simply scrolls through the sensors and indicates, by keystroke, for example, which of the available sensors to activate. Enablement of a sensor may key enablement of another related sensor or associated database or function. For example, enablement of the GPS receiver 448 preferably triggers enablement of a separate enter GIS route number, or enable GIS database, query operation 450, wherein a particular pre-programmed course, corresponding to the potential route the vehicle could travel, might be requested. The course data could have been previously stored in GIS format in the system computer database 212 or 308. Further, once the course has been chosen, the control system, reading position information from the GPS receiver, and relating this to the GIS data, may adjust the fluid material spread width to the known optimal dimensions and automatically deposit desired material types and amounts at the appropriate locations as the vehicle travels past the location.

It is envisioned that the set of sensors shown in FIG. 12B is not an exclusive list of possible sensors, but rather serves as an example of one possible series of sensors that a user may wish to have the opportunity to enable.

Once the available sensors have been configured, control transfers to operation 426 where the user is queried to edit the available single alert trigger or alert set points. See FIG. 12C. If the user desires to edit the set points, control transfers sequentially through operations 452–468 where the opportunity to edit each set point is provided. Each trigger point block corresponds either to an enabled sensor, or to one to the inherent, and thus always enabled, trigger points that correspond to the apparatus. Possible trigger points that are envisioned with this invention include: an air temperature alert set point 452, a wind speed alert set point 454, a wind direction alert set point 456, an air pressure alert set point 458, a humidity alert set point 460, a roadway surface temperature alert set point 462, a travel surface friction value alert set point 464, a road salt concentration alert set point 466 and a CMA concentration alert set point 468. If no editing of sensor set points is desired, control simply bypasses these operations, shown as line 413.

A user may wish to have alert set points triggered by a particular combination of incoming data from multiple sensors. Accordingly, after each individual single sensor set point has been entered in operations 452–468, the user is queried in operation 470 whether any combination alert set points are desired. If one or more combination set points is desired, operation 470 control transfers to a first combination alert set point block 472 in which a set point will be displayed for the first combination alert. The user will be queried in operation 474 as to whether the first combination alert set point should be edited. If the user gives an affirmative answer to query block 474, the user will be requested, in operation 476, to enter parameter (sensor) one and then in operation 478, enter the set alert value for parameter one, control then transfers to operation 480 where parameter two is identified and the set alert value for parameter two is inputted in operation 482. Once both parameters and their set alert values have been entered, the program will display the results in block operation 484. The user is queried whether to edit the displayed parameter combination in operation 486. An affirmative answer to this query will transfer, via line 488, back to block 476, where the user may edit parameter one by reentering the parameter one. The program will then proceed again through blocks 478, 480, 482, 484 and 486 until the user is satisfied with the displayed combination. When the user is satisfied with the displayed results by no further editing in operation 486, control transfers to operation 490 where the combination is stored.

Practically an unlimited number of parameter combination sets and corresponding alert set point values may be entered onto the system. Upon storing the first combination set point in operation 490 the program will display the next combination alert set point in operation 492. The user is then queried in operation 494 as to whether the displayed combination alert set point should be edited. An affirmative answer will transfer the user, via line 496 back to operation 476, to enter the parameter. The user will then proceed through the same operations 478–490 for this second combination as was performed for the first combination set point.

If the user does not wish to edit the second or next combination alert set point in operation 494, the program will query the user as to whether there is another combination set point contemplated in operation 498. An affirmative answer by the user will result in transfer back to operation 492 where the program displays a next combination alert set point. This procedure will continue until the user answers no to the query in operational block 498.

Once a negative response is entered at query block 498 control transfers to operation 500, where the user is queried as to whether a new and unique combination of alert set points is desired. If a new combination is requested the user is transferred, via line 502 back to operation 476, to enter parameter one of the combination, and the user may once again proceed through the steps to create a new combination set point pair. A negative response transfers the user, via line 428 in FIG. 12A to operation 501 where the user is queried whether to configure spreader and plow control.

Note, it is envisioned that parameter multiples of other than two may also be used by the system, thus a user may wish to enter combinations of three or more parameters that interact to give unique alert set point combinations. In this case, an additional set of operational blocks would be inserted between operations 482 and 484.

Once the user has either configured or by-passed the sensor system configuration, the set-up menu proceeds to query the user in operation 501 whether to configure a snow removal device such as the automatic spreader and plow control system 501. Each automatic spreader and plow configuration operational block will query the user as to whether a particular spreader or plow use should be enabled. Each query will allow the user to enter a yes or no as to enablement. If the user wishes to by-pass the spreader and plow configuration blocks, a negative answer at block 501 will cause the program to proceed directly to the vehicle operational block 505, as is shown by line 504. See FIG. 12A.

However, should the user desire to edit the configuration of the spreader and plow, control transfers from block 501 to the series of control operations, as is shown in FIG. 12E. The spreader and plow configuration blocks may include, but are not limited to enabling liquid fluid pump control in operation 506, enabling the solid fluid conveyance driver in operation 508, enabling the automatic spreader control system in operation 510 and enabling the automatic plow control system in operation 512. These spreader and plow uses and controls are described in more detail in my U.S. Pat. No. 5,904,296 issued May 18, 1999 and entitled APPARATUS AND SYSTEM FOR SYNCHRONIZED APPLICATION OF ONE OR MORE MATERIALS TO A SURFACE FROM A VEHICLE AND CONTROL OF A VEHICLE MOUNTED VARIABLE POSITION SNOW REMOVAL DEVICE. Once the user completes the spreader and plow configuration, program control transfers to automatic system via operation block 505, line 514.

Automatic System Operation block 505 is shown in more detail in FIG. 13. Automatic system operation begins in operational block 516 control then transfers to operation 518 where the system first polls all of the enabled and arrayed sensors, and then control transfers to operation 520 where the data from each sensor is compared with that sensor's set alert point. In the case where a combination of set points has been entered, the data collected from the combination of sensors is compared with the combination of alert set points in operation 522. Control then transfers to operation 524 where, if the GPS receiver is enabled, the sensor data can also be compared with the vehicle's current location, and/or read in conjunction with the GIS course information. Once all the sensor data has been collected and compared to the alert set points the vehicle sensor displays and alarms are updated in operation 526. Finally, the user is queried in operation 528 as to whether the automatic spreader control should be enabled. The user may choose to enable the automatic spreader control in operation 530 or exercise remote manual control over the spreader in operation 532.

The operation block 505 may be engaged automatically at discrete intervals during the operation of the vehicle, or may be engaged when the user determines a need to change or update the system during vehicle operation. It is also envisioned that the automatic spreader operations block could be by-passed by a manual override signal block 534. This block could be implemented by a manual override switch or button located on the dashboard of the vehicle. For example, this override control may be a spring loaded switch designed to simply suspend operations while the vehicle is negotiating an obstacle such as a new construction zone or other situation requiring direct operator input. The remote manual functioning of the system, indicated by operation 532, permits the system to continue to monitor all sensors and display information to the operator without exerting actual automatic control of the material dispensing apparatus and/or plow position. When the switch is released, automatic control resumes.

The present invention may be practiced otherwise than as specifically described above. Many changes, alternatives, variations, and equivalents to the various structures shown and described will be apparent to one skilled in the art. For example, there may be multiple computers and databases in various strategic locations linked together in order to implement an integrated monitoring and surface conditioning scheme. There may be a number of stationary weather monitoring sites as well as a number of vehicle mounted monitoring systems coupled to the computers to provide updated road and weather conditions and facilitate prediction of needed conditioning materials. Accordingly, the present invention is not intended to be limited to the particular embodiments illustrated but is intended to cover all such alternatives, modifications, and equivalents as may be included within the spirit and broad scope of the invention as defined by the following claims. All patents, patent applications, and printed publications referred to herein are hereby incorporated by reference in their entirety.

What is claimed is:

1. A method of controlling a material moving device connected with a vehicle, the material moving device being capable of moving through a plurality of positions, the method comprising:

receiving at least one geographic location signal;

determining a geographic location of the vehicle as a function of the operation of receiving the at least one geographic location signal; and moving the material moving device automatically to one of the plurality of positions as a function of the geographic location of the vehicle.

2. The method of claim 1 wherein the material moving device comprises at least one blade pivotally connected with the vehicle.

3. The method of claim 2 wherein the at least one blade is a front blade.

4. The method of claim 2 further comprising moving the at least one blade to one of the plurality of positions as a function of the geographic location of the vehicle.

5. The method of claim 2 wherein the blade comprises a movable side discharge blocking plate, and further comprising moving the side discharge blocking plate as a function of the geographic location of the vehicle.

6. The method of claim 4 further comprising changing a height of the blade as a function of the geographic location of the vehicle.

7. The method of claim 4 further comprising reorienting a discharge direction of the blade as a function of the geographic location of the vehicle.

8. The method of claim 1 wherein the at least one geographic location signal includes at least two geographic position signals.

9. The method of claim 1 wherein the material moving device is a road conditioning device.

10. The method of claim 1 wherein the material moving device is a snow removal device.

11. A method of determining a quantity of a road conditioning material to deposit on a vehicle travel surface having at least a first quantity of road conditioning material on the vehicle travel surface, the method comprising:

directing a first signal toward the vehicle travel surface;

receiving a second signal from the vehicle travel surface, the second signal being a function of the first signal; and determining the first quantity of road conditioning material on the vehicle travel surface as a function of the second signal.

12. The method of claim 11 further comprising:

depositing a second quantity of road conditioning material on the vehicle travel surface as a function of the operation of determining the first quantity of road conditioning material on the vehicle travel surface as a function of the second signal.

13. A method of determining a quantity of a road conditioning material to deposit on a vehicle travel surface comprising:

depositing a first quantity of road conditioning material on the vehicle travel surface;

directing a first signal toward the vehicle travel surface;

receiving a second signal from the vehicle travel surface, the second signal being a function of the first signal; and determining a remaining quantity of the first road conditioning material on the vehicle travel surface as a function of the second signal.

14. The method of claim 13 further comprising:

depositing a second quantity of road conditioning material on the vehicle travel surface as a function of the operation of determining a remaining quantity of the first road conditioning material on the vehicle travel surface as a function of the second signal.

15. The method of claim 14 wherein the operation of depositing a second quantity of road conditioning material on the vehicle travel surface occurs after the operation of depositing a first quantity of road conditioning material on the vehicle travel surface.

16. The method of claim 13 further comprising transmitting the remaining quantity of the first road conditioning material.

17. The method of claim 16 further comprising receiving a command to deposit a second quantity of road conditioning material on the vehicle travel surface as a function of the operation of transmitting.

18. An apparatus for determining a quantity of a road conditioning material to deposit on a vehicle travel surface comprising:

an electromagnetic radiation transmitter for transmitting a first signal toward a material from the vehicle travel surface;

an electromagnetic radiation receiver adapted to receive a second signal, wherein the second signal is a function of an interaction between the first signal and the material from the vehicle travel surface; and at least one processor connected to the electromagnetic radiation receiver, wherein the at least one processor is adapted to process the second signal and produce at least one output signal corresponding with the quantity of road conditioning material to deposit on the vehicle travel surface.

19. The apparatus of claim 18 wherein the material is on the vehicle travel surface.

20. The apparatus of claim 19 wherein the material from the vehicle travel surface comprises at least a preexisting quantity of road conditioning material.

* * * * *